(12) United States Patent
Serradeil Albalat et al.

(10) Patent No.: US 7,220,883 B2
(45) Date of Patent: May 22, 2007

(54) PROCESS FOR THE PREPARATION OF PRIMARY AMINES

(75) Inventors: Muriel Serradeil Albalat, Pertuis (FR); Jean-Claude Vallejos, Marseilles (FR); Christian Roussel, Aubagne (FR); Didier Wilhelm, Issy-les-Moulineaux (FR)

(73) Assignee: Clariant (France), Puteaux (FR)

( * ) Notice: Subject to any disclaimer, the term of this patent is extended or adjusted under 35 U.S.C. 154(b) by 192 days.

(21) Appl. No.: 10/523,734

(22) PCT Filed: Jul. 28, 2003

(86) PCT No.: PCT/IB03/03398

§ 371 (c)(1),
(2), (4) Date: Jan. 28, 2005

(87) PCT Pub. No.: WO2004/013081

PCT Pub. Date: Feb. 12, 2004

(65) Prior Publication Data

US 2005/0240059 A1 Oct. 27, 2005

(30) Foreign Application Priority Data

Jul. 30, 2002 (FR) .................................. 02 09674

(51) Int. Cl.
*C07C 209/42* (2006.01)
*C07D 249/08* (2006.01)
*C07D 249/14* (2006.01)

(52) U.S. Cl. .................... 564/413; 564/487; 548/264.8

(58) Field of Classification Search ...................... None
See application file for complete search history.

(56) References Cited

OTHER PUBLICATIONS

The Merck Index 12th edition (1996), BUDAVARI ed., Merck & Co., Inc., Whitehouse Station, NJ, p. 1029, entry No. 6095.*
PCT ISR for PCT/IP03/03398, Nov. 26, 2003.
Katritzky et al., "Synthesis & Highly Diastereoselective Alkylation of Chiral N- [(s,s)-3,5-Bis(1-methoxyethyl)-1,2,4-triazol-4-yl] arylimines" Tetrahedron: Assymetry, vol. 7, No. 6, pp. 1621-1630 (1996).
Enders et al., "Enantioselektive Syntheses von a-substituierten primaren Aminen durch nucleophile addition an SAMP-Hydrazone von Aldehyden," Agnew. Chem. 98, pp. 1118-1119 (1986).
Database Crossfire Beilstein Online. Beilstein Institut zur Forderung der Chemischen Wissenschaften, Frankfurt AM Main, DE XP002239352 (1988).
Pragst et al, "Investigations about the cleavage of some pyridinium & Triazolium Ions" J. Prakt. Chem. vol. 329, No. 6 pp. 1076-1086, XP0001091247 (1987).
Enders, "Alkylation of Chiral Hydrazones," Assymmetric Synthesis vol. 3, Academic Press Inc, pp. 275-338 (1984).
Pinner, "Ueber die Einwirkung von Hydrazin auf Imidoather," Chem Ber. pp. 984-1009 (1894).

Advanced Organic Chemistry, Reactions, Mechanisms and Structure, John Wiley & Sons, 4th ed. 6-35 pp. 934-935 (1992).
Advanced Organic Chemstry, Reactions,, Mechanisms, Structure; John Wiley & Sons 6-26, p. 918 (1992).
Advanced Organic Chemistry, Reactions, Mechanisms Structure; John Wiley & Sons 9-51, p. 1219 (1992.
Martinez-Diaz et al., "Preparation & Enantiomeric Purity Determination of New Chiral C2 Building Blocks Based on the 4-Amino-1,2,4-triazole Unit," Tetrahedron: Assymetry vol. 5. No. 7 pp. 1291-1296 (1994).
Matsuda et al, "Reaction of 4-Amino-1,2,4-Triazolium Salts w/ Polarized Olefins," Heterocycles, vol. 41, No. 12, pp. 2777-2784 (1995).
Alonzo et al., "Proton-Ionizable Macrocycles Containing 1,2,4-Triazole and 4-amino-1,2,4-triazole Subunits," Heterocycles, vol. 26, No. 4, pp. 989-1000 (1987).
Glover et al., "Sythesis of 1,1'-Dimethyl-4,4'-azo-1,2,4-triazolium and 3,3'-Dimehtyl-1,1'-azobenzotriazolium Salts," J. Chem. Soc. Perkins Trans. 1 pp. 1792-1794 (1974).
Becker et al.., "Azocoupling of Quaternary 1,2,4-Triazolium Salts to form 5-p-N,N-Dimethylaminophenylazo-1,2,4-triazolium Salts," Journal fur Praktische Chemie 330 pp. 325-337 (1988).
Alcalde et al., "Non-classical [1₄] Metaheterophanes Containing Betaine Units. Synthesis NMR Spectroscopy & X-Ray Crystallography," J. Chem. Soc., Chem. Commun pp. 1239-1240 (1995).
PCT International Preliminary Examination Report for PCT/IB03/03398, Jul. 19, 2004.
PCT Written Opinion for PCT/IB03/03398, mailed Mar. 23, 2004.

* cited by examiner

*Primary Examiner*—Brian Davis
(74) *Attorney, Agent, or Firm*—Anthony A. Bisulca

(57) ABSTRACT

Process for the preparation of primary amines of formula (I):

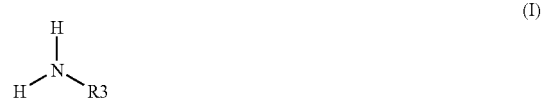

where R3 represents an alkyl, cycloalkyl or aralkyl group, by reaction of a triazolium salt of formula (II):

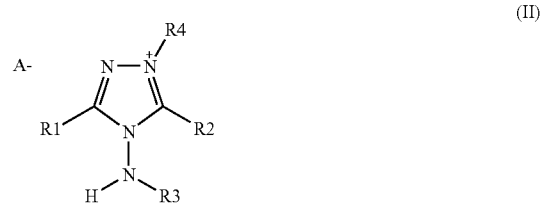

where R1 and R2 represent hydrogen or an alkyl, aralkyl or aryl group, R4 represents an alkyl or aralkyl group or a residue of an organic polymer functionalized by an alkylating group, and A⁻ represents a halogen, alkylsulphonate, arylsulphonate, alkyl sulphate, hydrogensulphate, hemisulphate, perchlorate or hydroxide, with a hydride, in order to obtain an amine of formula (I), which is isolated, if desired, and intermediates.

26 Claims, No Drawings

PROCESS FOR THE PREPARATION OF PRIMARY AMINES

CROSS REFERENCE TO RELATED APPLICATION

This application is a national stage application under 35 USC § 371 of Application No. PCT/IB0303398, having an international filing date of Jul. 28, 2003, the entire contents of which is hereby incorporated herein by reference.

The present invention relates to a process for the preparation of primary amines, of optically active primary amines and of novel intermediates useful for this purpose.

Primary amines and more particularly optically active primary amines are compounds which can be used in the preparation of medicaments, of plant-protection products and their intermediates or as resolving agents for optically active amines only.

While numerous methods exist for the synthesis of primary amines, few methods allow access to optically active primary amines.

It is known that these optically active amines can be prepared enzymatically. However, this method exhibits various disadvantages, such as the use of large amounts of enzyme, very long reaction times, dilute reaction media and complicated purification stages.

Another method is the optical resolution of a racemic mixture using, for example, an optically active acid. The major disadvantage of this process is the loss of 50% of the product.

Other methods have been used, such as the asymmetric hydrogenation of imines in the presence of a chiral ligand or the reduction of imines with an optically active alkali metal hydride. Finally, methods using a chiral inductor for asymmetric induction have been developed in order to access these optically active amines, such as, for example, the methodology developed by Enders (in Asymmetric Synthesis, edited by Morrison J. D., Academic, Orlando (1984); Vol. 3B, p. 275) with the chiral auxiliaries SAMP, (S)-1-Amino-2-(Methoxymethyl)Pyrrolidine, and RAMP, (R)-1-Amino-2-(Methoxymethyl)-Pyrrolidine.

Nevertheless, these various methods use reactants which are expensive and difficult to prepare.

It would therefore be desirable to have available a process for the preparation of optically active primary amines which makes it possible to solve the above problems while starting from commercially available and inexpensive materials.

Katritzky, A. R. et all. (Tetrahedron: Asymmetry, (1996), Vol. 7, No. 6, 1621–1630) describes the use of the chiral synthon (S,S)-4-amino-3,5-bis(1-hydroxyethyl)-1,2,4-triazole, prepared from (S)-lactic acid and hydrazine hydrate, in diastereoselective alkylation reactions on CN bonds of hydrazones but the release of the chiral amines is not described.

The Applicant Company has discovered that the reaction of a triazolium salt, derived from 4-amino-1,2,4-triazole synthons, with a hydride results in primary amines or optically active primary amines without epimerization of the stereogenic centre.

This is why a subject-matter of the present application is a process for the preparation of primary amines of formula (I):

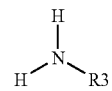

in which

R3 represents a linear or branched alkyl group including from 1 to 6 carbon atoms which is optionally substituted by one or more hydroxyl groups, amino groups, alkoxy groups including from 1 to 6 carbon atoms or aryl groups including from 6 to 10 carbon atoms, the aryl groups optionally being substituted by one or more linear or branched alkyl groups including from 1 to 6 carbon atoms or by one or more alkoxy groups including from 1 to 6 carbon atoms or by one or more phenyl groups, a cycloalkyl group including from 5 to 7 carbon atoms which is optionally substituted by one or more linear or branched alkyl groups including from 1 to 6 carbon atoms or by one or more alkoxy groups including from 1 to 6 carbon atoms, an aralkyl group including from 7 to 16 carbon atoms which is optionally substituted by one or more linear or branched alkyl groups including from 1 to 6 carbon atoms, by one or more alkoxy groups including from 1 to 6 carbon atoms or by one or more phenyl groups, by reaction of a triazolium salt of formula (II):

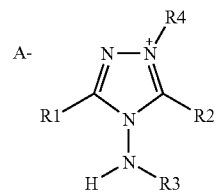

in which

R1 and R2, which are identical or different, represent hydrogen, a linear or branched alkyl group including from 1 to 6 carbon atoms which is optionally substituted by one or more alkoxy groups including from 1 to 6 carbon atoms, —(OCH$_2$CH$_2$O)$_n$R'" groups in which n represents an integer ranging from 1 to 4 and R'" is a linear or branched alkyl group including from 1 to 4 carbon atoms, —O-aryl groups including from 6 to 10 carbon atoms which is optionally substituted by one or more alkoxy groups including from 1 to 6 carbon atoms, linear or branched alkyl groups including from 1 to 6 carbon atoms or phenyl groups, or —O-aralkyl groups including from 7 to 16 carbon atoms which is optionally substituted by one or more alkoxy groups including from 1 to 6 carbon atoms, linear or branched alkyl groups including from 1 to 6 carbon atoms or phenyl groups;

an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups;

an aryl group including from 6 to 10 carbon atoms which is optionally substituted by one or more alkoxy groups including from 1 to 6 carbon atoms or linear or branched alkyl groups including from 1 to 6 carbon atoms or phenyl groups, R3 has the meaning already indicated, R4 represents a linear or branched alkyl group including from 1 to 6 carbon atoms which is optionally substituted by a —COOH radical or a —COOR''' group in which R''' represents a linear or branched alkyl radical including from 1 to 4 carbon atoms, an aralkyl group including from 7 to 16 carbon atoms which is optionally substituted by one or more alkoxy groups including from 1 to 6 carbon atoms or linear or branched alkyl groups including from 1 to 6 carbon atoms or an —COOH radical or a —COOR''' group in which R''' represents a linear or branched alkyl radical including from 1 to 4 carbon atoms, a residue of an organic polymer functionalized by an alkylating group, A represents a halogen, an alkylsulphonate group including from 1 to 6 carbon atoms which is optionally substituted by one or more halogen groups, an arylsulphonate group including from 6 to 10 carbon atoms which is optionally substituted by one or more halogen groups or linear or branched alkyl groups including from 1 to 4 carbon atoms, an alkyl sulphate group including from 1 to 6 carbon atoms, a hydrogensulphate group, a hemisulphate group, a perchlorate group, a hydroxide group, with a hydride, to obtain the amine of formula (I), which is isolated, if desired.

Preferably, the R3 group comprises an asymmetric carbon α to the nitrogen.

In the present invention and subsequently, when R'', R'1, R'2, R1, R2, R4, R5, R6 or R7 represents a linear or branched alkyl radical including from 1 to 6 carbon atoms, it is, for example, a methyl, ethyl, propyl, isopropyl or butyl radical and preferably a methyl, ethyl, propyl or isopropyl radical.

When R3 represents a linear or branched alkyl radical including from 1 to 6 carbon atoms, it is, for example, a methyl, ethyl, propyl, isopropyl, butyl, isobutyl, sec-butyl, tert-butyl, pentyl, neopentyl, isopentyl, hexyl or isohexyl radical and preferably an ethyl, propyl, isopropyl, butyl or sec-butyl radical.

When R3 represents a cycloalkyl group including from 5 to 7 carbon atoms, it is, for example, a cyclopentyl or cyclohexyl radical.

When R5, R6 or R7 represents a cycloalkyl group including from 3 to 7 carbon atoms, it is, for example, a cyclopropyl, cyclobutyl, cyclopentyl or cyclohexyl radical and preferably a cyclopentyl or cyclohexyl radical.

When R'', R'1, R'2, R1, R2, R5, R6 or R7 represents an aryl group including from 6 to 10 carbon atoms, it is, for example, a phenyl or naphthyl radical and preferably a phenyl radical.

When R'', R'1, R'2, R1, R2, R3, R4, R5, R6 or R7 represents an aralkyl group including from 7 to 16 carbon atoms, it is, for example, a benzyl, phenylethyl, phenylpropyl, phenylbutyl, 1- or 2-naphthylmethyl, 1- or 2-naphthylethyl, 1- or 2-naphthylpropyl or 1- or 2-naphthylbutyl radical and preferably a benzyl or phenylethyl radical.

When R''' or R'''' represents a linear or branched alkyl radical including from 1 to 4 carbon atoms, it is, for example, a methyl, ethyl, propyl or butyl radical and preferably a methyl or ethyl radical.

When R4 represents a residue of an organic polymer functionalized by an alkylating group, it is, for example, a polystyrene or poly(styrene-co-divinylbenzene) residue and preferably a polystyrene residue.

When A represents an alkylsulphonate group including from 1 to 6 carbon atoms, it is, for example, a methylsulphonate, ethylsulphonate or propylsulphonate radical and preferably a methylsulphonate or ethylsulphonate radical.

When A represents an arylsulphonate group including from 6 to 10 carbon atoms, it is, for example, a phenylsulphonate or naphthylsulphonate radical and preferably a phenylsulphonate radical.

When A represents an alkyl sulphate group including from 1 to 6 carbon atoms, it is, for example, a methyl sulphate, ethyl sulphate, propyl sulphate or butyl sulphate radical and preferably a methyl sulphate or ethyl sulphate radical.

When A represents a halogen, it is, for example, a Cl, Br, F or I radical and preferably a Cl or Br radical.

In the present invention and subsequently, as regards the substituents, the term "linear or branched alkyl radical including from 1 to 6 carbon atoms" denotes, for example, a methyl, ethyl, propyl, isopropyl, butyl, isobutyl, sec-butyl, tert-butyl or pentyl radical and preferably a methyl, ethyl, propyl, isopropyl, butyl, isobutyl, sec-butyl or tert-butyl radical; the term "linear or branched alkyl radical including from 1 to 4 carbon atoms" denotes, for example, a methyl, ethyl, propyl, isopropyl, butyl or tert-butyl radical and preferably a methyl, ethyl, propyl or isopropyl radical; the term "alkoxy radical including from 1 to 6 carbon atoms" denotes, for example, a methoxy, ethoxy, propoxy or butoxy radical and preferably a methoxy or ethoxy radical; the term "—O-aryl including from 6 to 10 carbon atoms" denotes, for example, a phenoxy or naphthoxy radical and preferably a phenoxy radical; the term "—O-aralkyl including from 7 to 16 carbon atoms" denotes, for example, a benzyloxy or naphthylmethyloxy radical and preferably a benzyloxy radical.

Under preferred conditions of implementation of the process described above, the reaction of the triazolium salt of formula (II) with a hydride is generally carried out in an inert solvent, such as THF, at a temperature of between 0° C. and 200° C., preferably between ambient temperature and the boiling point of the reaction medium, in particular for a period of time of between 1 h and 24 h.

Mention may be made, as examples of hydrides, of diisobutylaluminium hydride (DIBAL-H), lithium aluminium hydride (LiAlH$_4$), sodium borohydride (NaBH$_4$), poly-(methylhydrosiloxane) (PMHS), sodium triacetoxyborohydride (NaBH(OAc)$_3$), sodium trimethoxyborohydride (NaBH(OCH$_3$)$_3$) or lithium borohydride (LiBH$_4$) and preferably lithium borohydride (LiBH$_4$).

Under preferred conditions of implementation of the process described above, the triazolium salt of formula (II) corresponds to the formula (IIa):

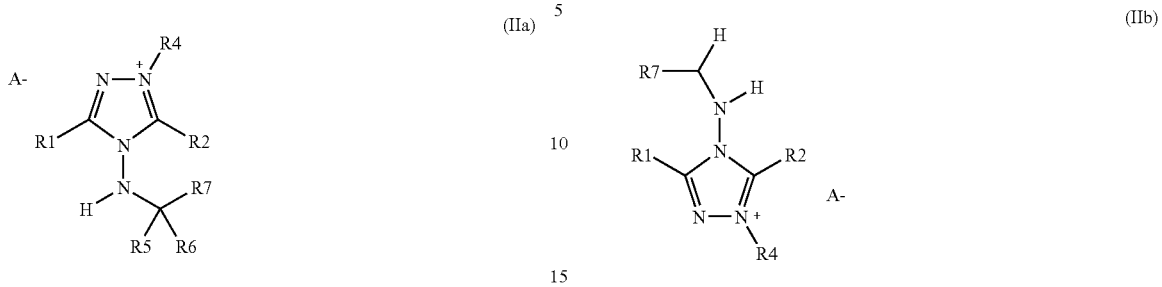

in which
R1, R2, R4 and A have the meaning already indicated and
R5 represents
a hydrogen,
a linear or branched alkyl group including from 1 to 6 carbon atoms which is optionally substituted by one or more alkoxy groups including from 1 to 6 carbon atoms, hydroxyl groups or amino groups,
a cycloalkyl group including from 3 to 7 carbon atoms which is optionally substituted by one or more alkoxy groups including from 1 to 6 carbon atoms or linear- or branched alkyl groups including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups,
R6 represents
a linear or branched alkyl group including from 1 to 6 carbon atoms which is optionally substituted by one or more alkoxy groups including from 1 to 6 carbon atoms, hydroxyl groups or amino groups,
a cycloalkyl group including from 3 to 7 carbon atoms which is optionally substituted by one or more alkoxy groups including from 1 to 6 carbon atoms or linear or branched alkyl groups including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups,
an aminotriazolium group of formula in which R1, R2, R4 and A have the meaning already indicated,
R7 represents
a hydrogen,
a linear or branched alkyl group including from 1 to 6 carbon atoms which is optionally substituted by one or more alkoxy groups including from 1 to 6 carbon atoms, hydroxyl groups or amino groups,
a cycloalkyl group including from 3 to 7 carbon atoms which is optionally substituted by one or more alkoxy groups including from 1 to 6 carbon atoms or linear or branched alkyl groups including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms or linear or branched alkyl groups including from 1 to 6 carbon atoms or phenyl groups, or
R5 and R6 can form, together with the carbon atom to which they are bonded, a ring comprising 5 to 7 carbon atoms which is optionally substituted by one or more alkoxy groups including from 1 to 6 carbon atoms or linear or branched alkyl groups including from 1 to 6 carbon atoms,
it being understood that the carbon carrying the R5, R6 and R7 radicals must be asymmetric.

Under yet other preferred conditions for the implementation of the process described above, the compound of formula (II) corresponds to the formula (IIa) defined above and, in addition, the said compound of formula (IIa) is prepared by reaction of a compound of formula (III):

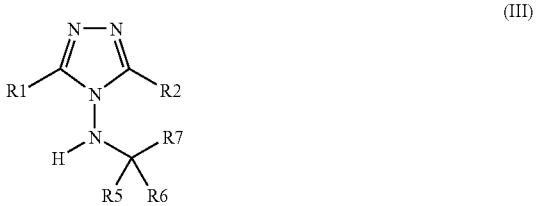

in which R1, R2, R5, R6 and R7 have the meaning indicated above, with an agent for the quaternization of a nitrogen, to produce the compound of formula (IIa), which is isolated, if desired, or which is employed directly in the following stage.

Under still other preferred conditions for the implementation of the process described above, the compound of formula (II) corresponds to the formula (IIa) defined above and, in addition, the said compound of formula (IIa) is prepared by reaction of a compound of formula (IIIa):

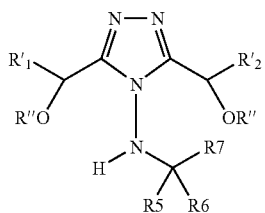

(IIIa)

in which R5, R6 and R7 have the meaning already indicated, R'1 and R'2 represent a linear or branched alkyl group including from 1 to 6 carbon atoms which is optionally substituted by one or more alkoxy groups including from 1 to 6 carbon atoms, an aryl group including from 6 to 10 carbon atoms which is optionally substituted by one or more alkoxy groups including from 1 to 6 carbon atoms or linear or branched alkyl groups including from 1 to 6 carbon atoms or phenyl groups, or an aralkyl group including from 7 to 16 carbon atoms which is optionally substituted by one or more alkoxy groups including from 1 to 6 carbon atoms or linear or branched alkyl groups including from 1 to 6 carbon atoms or phenyl groups, and R" represents hydrogen, a linear or branched alkyl group including from 1 to 6 carbon atoms, an aryl group including from 6 to 10 carbon atoms which is optionally substituted by one or more alkoxy groups including from 1 to 6 carbon atoms or linear or branched alkyl groups including from 1 to 6 carbon atoms or phenyl groups, an aralkyl group including from 7 to 16 carbon atoms which is optionally substituted by one or more alkoxy groups including from 1 to 6 carbon atoms or linear or branched alkyl groups including from 1 to 6 carbon atoms or phenyl groups, a —(CH$_2$CH$_2$O)$_n$R'" group in which n represents an integer ranging from 1 to 4 and R'" is a linear or branched alkyl group including from 1 to 4 carbon atoms, with an agent for the quaternization of a nitrogen, to produce the compound of formula (IIa), which is isolated, if desired, or which is employed directly in the following stage.

Under preferred conditions for the implementation of the process described above, the reaction of the compound of formula (III) or of formula (IIIa) with an agent for the quaternization of a nitrogen is carried out by application or adaptation of the methods described in the literature, such as: Pinner, A., Chem. Ber., (1894), 27, 1006; Glover, E. E. et al., J. Chem. Soc. Perkin Trans. 1, (1974), 1792–1794; Becker, H. G. O. et al., J. Prakt. Chem., (1988), 330, 325–337; Matsuda, Y. et al., Heterocycles, (1995), 41, 2777–2784; Alcade, E. et al., J. Chem. Soc., Chem. Commun., (1995), 1239–1240. This reaction is generally carried out by adding, under a dry atmosphere, an equimolar amount or a slight excess of the agent for the quaternization of a nitrogen, with stirring, to the compound of formula (III) or of formula (IIIa), with the optional use of an inert solvent, preferably THF, at ambient temperature or while heating, for a period of time of between 1 h and 48 h.

The compounds of formula (III) or of formula (IIIa) can be quaternized with agents for the quaternization of a nitrogen known to a person skilled in the art, including, for example, methyl iodide, ethyl chloride, ethyl bromide, dimethyl sulphate, diethyl sulphate, benzyl bromide or α-phenylethyl bromide.

The ions denoted A$^-$ in the compounds of formula (II) or (IIa) are obtained by the action of agents for the quaternization of a nitrogen or can be obtained by conventional methods for exchanges of anions.

Under still other preferred conditions for the implementation of the process described above, the compound of formula (IIIa) is additionally prepared by reaction of an organometallic compound of formula

R7-M in which R7 has the meaning already indicated above and M represents an MgX or CeX$_2$ group in which X represents a halogen atom or M represents a metal, such as Li, Cu or (½) Zn, with a compound of formula (IV)

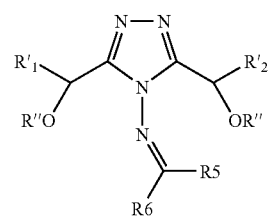

(IV)

in which R'1, R'2, R", R5 and R6 have the meaning already indicated, it being understood that, when R" is a hydrogen, at least one of R5 and R6 is an optionally substituted aryl group, to produce the compound of formula (IIIa), which is isolated, if desired, or which is employed directly in the following stage.

Under preferred conditions for the implementation of the process described above, the reaction of the organometallic compound of formula R7-M with a compound of formula (IV) is carried out by application or adaptation of the methods described in Advanced Organic Chemistry, Reactions, Mechanisms, and Structure, John Wiley & Sons, 4th edition, 6–35, pages 934–935, and the references cited. This reaction is generally carried out by using between 2 and 10 equivalents of the compound R7-M with respect to the compound of formula (IV), under an inert atmosphere, in an inert solvent (THF, ether, toluene or dichloromethane, for example), at a temperature of between −100° C. and ambient temperature, for a period of time of between 1 h and 24 h.

Under still other preferred conditions for the implementation of the process described above, the compound of formula (IV) is prepared by etherification and reaction of a compound of formula (V):

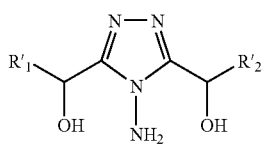

in which R'1 and R'2 have the meaning already indicated above, with a compound of formula

in which R5 and R6 have the meaning already indicated, to produce the compound of formula (IV), which is isolated, if desired, or which is employed directly in the following stage.

Under preferred conditions for the implementation of the process described above, the reaction of a compound of formula (V) with a compound of formula O=CR5R6 is carried out by using an equimolar amount or a slight excess of one of the two reactants in a solvent, if necessary (toluene, cyclohexane or 1,2-dichloroethane, for example), optionally using an acid catalyst, such as para-toluenesulphonic acid or methane-sulphonic acid, at a temperature of between ambient temperature and the boiling point of the reaction medium, for a period of time of between 1 h and 24 h, optionally with azeotropic removal of the water.

The etherification is carried out by application or adaptation of the methods described by: Katritzky, A. R. et al., Tetrahedron: Asymmetry, (1996), 7, 1621–1630.

The etherification can take place before the reaction of the compound of formula (V) with the compound of formula O=CR5R6. It can also take place after the reaction of the compound of formula (V) with the compound of formula

it being understood that at least one of R5 and R6 represents an optionally substituted aryl group.

The compounds of formula (V) are known in the literature and can be prepared by application or adaptation of the methods described by Martinez-Diaz, M. V. et al., Tetrahedron: Asymmetry, (1994), 5, 1291–1296; Alonso, J. M. et al., J. Heterocycles, (1987), 26, 989–1000.

Under yet other preferred conditions for the implementation of the process described above, the compound of formula (IIa) is additionally prepared by the action of an alkali metal hydride, such as lithium borohydride or sodium borohydride, on a compound of formula (IV) defined above or by hydrogenation of the said compound of formula (IV), it being understood that R5 cannot, in this case, represent hydrogen.

Under preferred conditions for the implementation of the process described above, the reduction of a compound of formula (IV) by the action of an alkali metal hydride is carried out by application or adaptation of the methods described in Advanced Organic Chemistry, Reactions, Mechanisms, and Structure, John Wiley & Sons, 4th edition, 6–26, page 918, and 9–51, page 1219, and the references cited. This reduction is generally carried out by using an equimolar amount or a slight excess of alkali metal hydride in a solvent (THF or MeOH, for example), at a temperature of between ambient temperature and the boiling point of the reaction medium, for a period of time of between 1 h and 24 h.

Under preferred conditions for the implementation of the process described above, the reduction of a compound of formula (IV) by hydrogenation is carried out with a catalyst (Raney nickel, for example), in a solvent, such as methanol or ethanol, under a hydrogen pressure from $10^5$ Pa (1 bar) to $50 \times 10^5$ Pa (50 bar), at ambient temperature or while heating, and for a period of time of between 1 h and 2 days.

The reaction of the compounds of formula (II) with a hydride makes possible the synthesis of optically active primary amines without epimerization of the stereogenic centre if the compounds of formula (II) are optically pure.

These properties justify the use of the compounds of formula (IIIa) described above, which are precursors of the compounds of formula (II), in the implementation of a process described above.

Another subject-matter of the present application is therefore novel intermediates for preparing an amine of formula $H_2N$—CR5R6R7, namely the compounds of formula (IIIa)

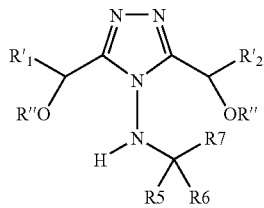

in which
R'1 and R'2 represent methyl groups,
R" represents
a linear or branched alkyl group including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups,
or a —$(CH_2CH_2O)_n R'''$ group in which n represents an integer ranging from 1 to 4 and R''' is a linear or branched alkyl group including from 1 to 4 carbon atoms,
R5 represents
a hydrogen,
a linear or branched alkyl group including from 1 to 6 carbon atoms which is optionally substituted by one or more alkoxy groups including from 1 to 6 carbon atoms, hydroxyl groups or amino groups,
a cycloalkyl group including from 3 to 7 carbon atoms which is optionally substituted by one or more alkoxy groups including from 1 to 6 carbon atoms or linear or branched alkyl groups including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups, R6 represents a linear or branched alkyl group including from 1 to 6 carbon atoms which is optionally substituted by one or more alkoxy groups including from 1 to 6 carbon atoms, hydroxyl groups or amino groups, a cycloalkyl group including from 3 to 7 carbon atoms which is optionally substituted by one or more alkoxy groups including from 1 to 6 carbon atoms or linear or branched alkyl groups including from 1 to 6 carbon atoms, an aryl group including from 6 to 10 carbon atoms which is optionally substituted by one or more alkoxy groups including from 1 to 6 carbon atoms or linear or branched alkyl groups including from 1 to 6 carbon atoms or phenyl groups, an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups, a —CH$_2$OR"" group in which R"" represents hydrogen, a linear or branched alkyl radical including from 1 to 4 carbon atoms or a benzyl radical, R7 represents a hydrogen, a linear or branched alkyl group including from 1 to 6 carbon atoms which is optionally substituted by one or more alkoxy groups including from 1 to 6 carbon atoms, hydroxyl groups or amino groups, a cycloalkyl group including from 3 to 7 carbon atoms which is optionally substituted by one or more alkoxy groups including from 1 to 6 carbon atoms or linear or branched alkyl groups including from 1 to 6 carbon atoms, an aryl group including from 6 to 10 carbon atoms which is optionally substituted by one or more alkoxy groups including from 1 to 6 carbon atoms or linear or branched alkyl groups including from 1 to 6 carbon atoms or phenyl groups, an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups, or R5 and R6 can form, together with the carbon atom to which they are bonded, a ring comprising from 5 to 7 carbon atoms which is optionally substituted by one or more alkoxy groups including from 1 to 6 carbon atoms or linear or branched alkyl groups including from 1 to 6 carbon atoms, it being understood that the carbon carrying the R5, R6 and R7 radicals must be asymmetric, with the exception of the following compounds of formula (IIIa):

| R'1, R'2 | R" | R5 | R7 | R6 |
|---|---|---|---|---|
| CH$_3$ | CH$_3$ | H | Phenyl | p-Toluene |
| CH$_3$ | CH$_3$ | H | CH$_2$CH$_2$-Phenyl | p-Cl-Phenyl |
| CH$_3$ | CH$_3$ | H | CH$_2$CH$_2$-Phenyl | Phenyl |
| OH$_3$ | CH$_3$ | H | CH$_2$-Phenyl | p-Cl-Phenyl |
| CH$_3$ | CH$_3$ | H | CH$_2$-Phenyl | Phenyl |
| CH$_3$ | CH$_3$ | H | p-Toluene | p-Cl-Phenyl | and preferably with the exception of any other compound of the known prior art.

A further subject-matter of the present application is novel intermediates for preparing an amine of formula H$_2$N—CR5R6R7, namely the following compounds of formula (IIIb):

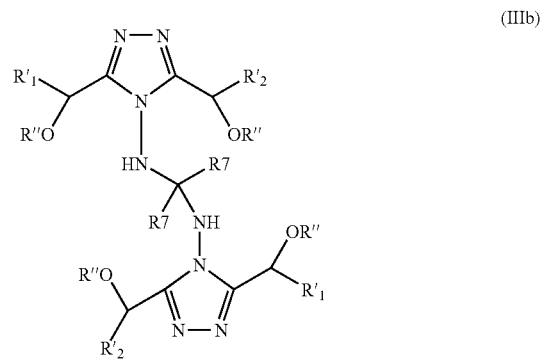

(IIIb)

in which R'1 and R'2 represent methyl groups,

R" represents a linear or branched alkyl group including from 1 to 6 carbon atoms, a group of the —(CH$_2$CH$_2$O)$_n$R''' type where n=1, 2, 3 or 4 and where R''' represents a linear or branched alkyl group including from 1 to 4 carbon atoms, an aryl group including from 6 to 10 carbon atoms which is optionally substituted by one or more alkoxy groups including from 1 to 6 carbon atoms or linear or branched alkyl groups including from 1 to 6 carbon atoms or phenyl groups, an aralkyl group including from 7 to 16 carbon atoms which is optionally substituted by one or more alkoxy groups including from 1 to 6 carbon atoms or linear or branched alkyl groups including from 1 to 6 carbon atoms or phenyl groups, and R7 has the meaning already indicated.

Another subject-matter of the present application is novel intermediates for preparing an amine of formula H$_2$N—CHR6R7, namely the following compounds of formula (IIIa):

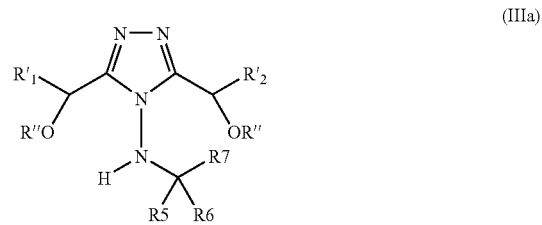

(IIIa)

4-[(S)-1-Ethyl-2,2-dimethoxyethylamino]-(S,S)-3,5-bis(1-methoxyethyl)-1,2,4-triazole 4-[(R)-1-Ethyl-2,2-dimethoxyethylamino]-(S,S)-3,5-bis(1-methoxyethyl)-1,2,4-triazole 4-[(S)-1-Ethyl-2,2-dimethoxyethylamino]-(S,S)-3,5-bis(1-ethoxyethyl)-1,2,4-triazole 4-[(R)-1-Ethyl-2,2-dimethoxyethylamino]-(S,S)-3,5-bis(1-ethoxyethyl)-1,2,4-triazole 4-(1-Phenyl-2,2-dimethoxyethylamino)-(S,S)-3,5-bis(1-methoxyethyl)-1,2,4-triazole
4-(1-Ethyl-2,2-dimethoxyethylamino)-(S,S)-3,5-bis(1-(2-methoxyethyl)ethyl)-1,2,4-triazole
4-(1-Ethylbutylamino)-(S,S)-3,5-bis(1-methoxyethyl)-1,2,4-triazole
4-(1-Ethylisobutylamino)-(S,S)-3,5-bis(1-methoxyethyl)-1,2,4-triazole
4-(1-Phenylpropylamino)-(S,S)-3,5-bis(1-methoxyethyl)-1,2,4-triazole
4-(1-Phenylethylamino)-(S,S)-3,5-bis(1-methoxyethyl)-1,2,4-triazole
(Hexyl-3,4-diamino)-4,4'-bis[(S,S)-3,5-bis(1-methoxyethyl)-1,2,4-triazole].

Another subject-matter of the present application is novel intermediates for preparing an amine of formula H$_2$N—CR5R6R7, namely the following compounds of formula (IV):

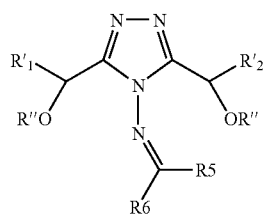

in which R'1 and R'2 represent methyl groups,
R" represents
hydrogen,
a linear or branched alkyl group including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups, or
a —(CH$_2$CH$_2$O)$_n$R'" group in which n represents an integer ranging from 1 to 4 and R'" is a linear or branched alkyl group including from 1 to 4 carbon atoms,
R5 represents
a hydrogen,
a linear or branched alkyl group including from 1 to 6 carbon atoms which is optionally substituted by one or more alkoxy groups including from 1 to 6 carbon atoms, hydroxyl groups or amino groups,
a cycloalkyl group including from 3 to 7 carbon atoms which is optionally substituted by one or more alkoxy groups including from 1 to 6 carbon atoms or linear or branched alkyl groups including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups, R6 represents
a linear or branched alkyl group including from 1 to 6 carbon atoms which is optionally substituted by one or more alkoxy groups including from 1 to 6 carbon atoms, hydroxyl groups or amino groups,
a cycloalkyl group including from 3 to 7 carbon atoms which is optionally substituted by one or more alkoxy groups including from 1 to 6 carbon atoms or linear or branched alkyl groups including from 1 to 6 carbon atoms,
an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups,
a —CH$_2$OR"" group in which R"" represents an alkyl radical including from 1 to 4 carbon atoms or a benzyl radical, or
R5 and R6 can form, together with the carbon atom to which they are bonded, a ring comprising 5 to 7 carbon atoms which is optionally substituted by one or more alkoxy groups including from 1 to 6 carbon atoms or linear or branched alkyl groups including from 1 to 6 carbon atoms, it being understood that at least one of the R5 and R6 radicals is an optionally substituted aryl group, in the case where R" represents hydrogen, with the exception of the following compounds:

| R'1, R'2 | R" | R6 | R5 |
|---|---|---|---|
| CH$_3$ | H | p-Toluene | H |
| CH$_3$ | H | CH$_2$-Phenyl | H |
| CH$_3$ | H | Phenyl | H |
| CH$_3$ | H | p-Cl-Phenyl | H |
| CH$_3$ | H | o-Cl-Phenyl | H |
| CH$_3$ | H | Phenyl | Me |
| CH$_3$ | H | p-MeO-Phenyl | Me |
| CH$_3$ | H | m-Nitrophenyl | Me |
| CH$_3$ | H | Isopropyl | Me |
| CH$_3$ | H | tert-Butyl | Me |
| CH$_3$ | CH$_3$ | Phenyl | H |
| CH$_3$ | CH$_3$ | p-Cl-Phenyl | H |
| CH$_3$ | CH$_3$ | p-Toluene | H |
| CH$_3$ | C$_2$H$_5$ | Phenyl | H | and preferably with the exception of any other compound of the known prior art.

Another subject-matter of the present application is novel intermediates for preparing an amine of formula H$_2$N—CR5R6R7, namely the following compounds of formula (IVa):

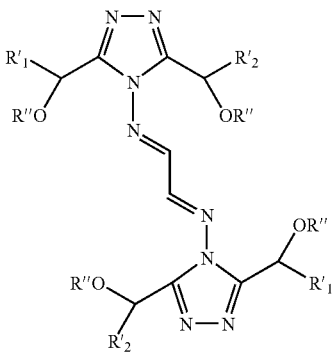

in which R'1 and R'2 represent methyl groups, and R" represents
- a linear or branched alkyl group including from 1 to 6 carbon atoms,
- an aryl group including from 6 to 10 carbon atoms which is optionally substituted by one or more alkoxy groups including from 1 to 6 carbon atoms or linear or branched alkyl groups including from 1 to 6 carbon atoms or phenyl groups,
- an aralkyl group including from 7 to 16 carbon atoms which is optionally substituted by one or more alkoxy groups including from 1 to 6 carbon atoms, linear or branched alkyl groups including from 1 to 6 carbon atoms or phenyl groups, or
- a $-(CH_2CH_2O)_nR'''$ group in which n represents an integer ranging from 1 to 4 and R''' is a linear or branched alkyl group including from 1 to 4 carbon atoms.

Another subject-matter of the present application is novel intermediates for preparing an amine of formula $H_2N-CR5R6R7$, namely the following compounds of formulae (IV) and (IVa):

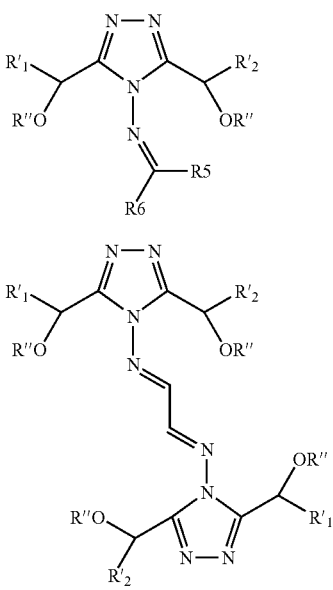

N-[(S,S)-3,5-Bis(1-methoxyethyl)-1,2,4-triazol-4-yl]-2,2-dimethoxyethylimine

N-[(S,S)-3,5-Bis(1-methoxyethyl)-1,2,4-triazol-4-yl]butylimine

N-[(S,S)-3,5-Bis(1-methoxyethyl)-1,2,4-triazol-4-yl]isobutylimine

N-[(S,S)-3,5-Bis(1-methoxyethyl)-1,2,4-triazol-4-yl]-1-(ethoxycarbonyl)methylimine N-[(S,S)3,5-Bis(1-methoxyethyl)-1,2,4-triazol-4-yl]-1-phenylethylimine N-[(S,S)-3,5-Bis(1-methoxyethyl)-1,2,4-triazol-4-yl]-1-methyl-2,2-dimethoxyethylimine Bis[N-[(S,S)-3,5-bis(1-methoxyethyl)-1,2,4-triazol-4-yl]methylimine]

N-[(S,S)-3,5-Bis(1-ethoxyethyl)-1,2,4-triazol-4-yl]-2,2-dimethoxyethylimine

N-[(S,S)-3,5-Bis(1-(2-methoxyethoxy)ethyl)-1,2,4-triazol-4-yl]-2,2-dimethoxyethylimine.

Under other preferred conditions for the implementation of the process described above, the stereoisomers of formula (III) or (IIIa) are separated by, optionally chiral, high performance liquid chromatography.

For this reason, another subject-matter of the present application is an enantiomerically pure stereoisomer of a compound of formula (III) or (IIIa) obtained according to the above process.

Under yet other preferred conditions for the implementation of the process described above, the diastereoisomers of formula (IIIa) are separated by crystallization after quaternization.

For this reason, another subject-matter of the present application is an enantiomerically pure diastereoisomer of a compound of formula (IIa) obtained according to the above process.

A further subject-matter of the present application is enantiomerically pure 1-benzyl-4-[(R)-1-phenyl-2,2-dimethoxyethylamino]-(S,S)-3,5-bis(1-methoxyethyl)-1,2,4-triazolium bromide.

A final subject-matter of the present application is the use of the intermediates described above in the manufacture of a primary amine of formula (I).

The preferred conditions for the implementation of the processes described above also apply to the other subject-matters of the invention which are targeted above, in particular to the intermediates.

The examples which follow illustrate the present application.

EXAMPLE 1

1-Phenyl-2,2-dimethoxyethylamine 6 ml of tetrahydrofuran (THF) and 3.5 mmol of 1-benzyl-4-(1-phenyl-2,2-dimethoxyethylamino)-(S,S)-3,5-bis(1-methoxyethyl)-1,2,4-triazolium bromide are introduced into a 100 ml round-bottomed flask equipped with a reflux condenser and a magnetic stirrer and then 1.75 ml of a 2 mol/l solution of lithium borohydride in THF are added at ambient temperature over a period of 1 to 2 h approximately. The reaction medium is subsequently left stirring at ambient temperature for 3 h and then brought to reflux for 3 h. After returning to ambient temperature, 20 ml of a 20% aqueous sodium hydroxide solution are added and then the aqueous phase is extracted with dichloromethane. The resulting organic phase is dried over anhydrous magnesium sulphate and then concentrated. The amine is purified by distillation. 0.19 g of the expected compound is obtained.

$^1$H NMR (CDCl$_3$): δ 3.27 (s, 3H, CH$_3$), 3.46 (s, 3H, CH$_3$), 4.04 (d, J=6.2 Hz, 1H, CH), 4.33 (d, J=6.2 Hz, 1H, CH), 7.33–7.45 (m, 5H, H$_{aromatic}$) ppm. $^{13}$C NMR (CDCl$_3$): δ 55.26 (CH$_3$), 55.62 (CH$_3$), 57.99 (CH), 108.79 (CH), 125.39–128.74 (CH$_{aromatic}$), 141.28 (C$_{aromatic}$) ppm. T$_{bp}$=108° C. under 400 Pa (3 mmHg)

EXAMPLE 2

1-Ethyl-2,2-dimethoxyethylamine

The compound is prepared as in Example 1 but using 1-benzyl-4-(1-ethyl-2,2-dimethoxyethylamino)-(S,S)-3,5-bis(1-methoxyethyl)-1,2,4-triazolium bromide. The amine is purified by distillation. 0.45 g of the expected compound is obtained.

$^1$H NMR (CDCl$_3$): δ 0.99 (t, J=7.5 Hz, 3H, CH$_3$), 1.65 (m, 2H, CH$_2$), 2.99 (m, 1H, CH), 3.40 (s, 3H, CH$_3$), 3.43 (s, 3H, CH$_3$), 4.28 (d, J=5.4 Hz, 1H, CH), 6.2 (s, 2H, NH$_2$) ppm. $^{13}$C NMR (CDCl$_3$): δ 10.35 (CH$_3$), 21.14 (CH$_2$), 54.08 (CH), 54.68 (CH$_3$), 54.84 (CH$_3$), 108.25 (CH) ppm. T$_{bp}$=62–63° C. under 2666.4 Pa (20 mmHg)

EXAMPLE 3

1-Benzyl-4-[(R)-1-phenyl-2,2-dimethoxyethylamino]-(S,S)-3,5-bis(1-methoxyethyl)-1,2,4-triazolium bromide (Quaternization of a Compound of Formula (IIIa))

1.5 g of 4-[(R)-1-phenyl-2,2-dimethoxyethylamino]-(S,S)-3,5-bis(1-methoxyethyl)-1,2,4-triazole and 0.6 g of benzyl bromide are introduced into a round-bottomed flask equipped with a magnetic stirrer and a calcium chloride drying tube. The reaction medium is left stirring at ambient temperature for approximately 48 h. 3 ml of THF are subsequently added and the mixture is filtered. The solid obtained is recrystallized from THF.

[α]$^{25}_D$=−143.700 (c=1.137, CHCl$_3$) M.p.=170–172° C. $^1$H NMR (CDCl$_3$): δ0.44 (d, J=6.8 Hz, 3H, CH$_3$), 1.84 (d, J=6.6 Hz, 3H, CH$_3$), 3.23 (s, 3H, CH$_3$), 3.43 (s, 3H, CH$_3$), 3.59 (s, 3H, CH$_3$), 3.75 (s, 3H, CH$_3$), 4.71 (d, J=7.6 Hz, 1H, CH), 4.90 (m, 2H, CH), 5.50 (m, 3H, CH$_2$+CH), 7.13–7.41 (m, 10H, H$_{aromatic}$), 8.33 (s, 1H, NH) ppm. $^{13}$C NMR (CDCl$_3$): δ 14.85 (CH$_3$), 18.57 (CH$_3$), 54.16 (CH$_3$), 55.03 (CH$_2$), 55.67 (CH$_3$), 57.52 (CH$_3$), 59.98 (CH$_3$), 67.25 (CH), 68.39 (CH), 69.18 (CH), 104.98 (CH), 127.52–129.19 (CH$_{aromatic}$), 132.27 (C$_{aromatic}$), 136.65 (C$_{aromatic}$), 156.03 (N—C=N), 158.08 (N—C=N) ppm.

EXAMPLE 4

4-[1-Methyl-2,2-dimethoxyethylamino]-(S,S)-3,5-bis(1-methoxyethyl)-1,2,4-triazole (Treatment of a Compound of Formula (IV) with an Organometallic Compound)

0.86 g of cerium chloride is introduced under nitrogen into 30 ml of tetrahydrofuran in a 100 ml three-necked flask equipped with a magnetic stirrer and a reflux condenser. This mixture is stirred at ambient temperature for 30 min and then under ultrasound for a further 30 min. After halting the ultrasound treatment, the reaction medium is brought to a temperature of −78° C. (ethanol/liquid nitrogen bath). At this temperature, 6.5 ml of a 1.6M methyllithium solution is added over approximately 15 min. The medium is then maintained at a temperature of −78° C. for 1 h. The temperature of the reaction medium is subsequently brought to a temperature of 0° C. over approximately 10 min. The reaction medium is then again brought to −78° C. At this temperature, 1 g of N-[(S,S)-3,5-bis(1-methoxyethyl)-1,2,4-triazol-4-yl]-2,2-dimethoxyethylimine, in solution in 10 ml of tetrahydrofuran, is added over 1 h. At the end of this addition, the temperature is maintained at −78° C. for 2 h and then the reaction medium is brought back to ambient temperature overnight. The reaction medium is poured onto a saturated aqueous ammonium chloride solution. The aqueous phase is extracted several times with ethyl acetate and the organic phases are combined; the resulting organic phase is dried over anhydrous magnesium sulphate before being concentrated. 0.8 g of the expected compound is obtained.

$^1$H NMR (CDCl$_3$): Presence of the two diastereoisomers, split or overlapping signals: δ 0.85 (d, J, 3H, CH$_3$), 1.5 (d, J, 6H, CH$_3$), 3.1–3.3 (m, 12+1H, CH$_3$+CH), 4.1 (d, J, 1H, CH), 4.5–4.8 (q, J, 2H, CH), 5.3 (d, J, 1H, NH) ppm. $^{13}$C NMR (CDCl$_3$): δ 13.27–13.62 (CH$_3$), 17.14–20.06 (CH$_3$), 54.17–57.3 (CH$_3$), 69.21–69.77 (CH), 106.027–106.297 (CH), 154.78–155.10 (N—C=N) ppm.

EXAMPLE 5

4-[(R and S)-1-Ethyl-2,2-dimethoxyethylamino]-(S,S)-3,5-bis(1-methoxyethyl)-1,2,4-triazole (Treatment of a Compound of Formula (IV) with an Organometallic Compound)

1 g of N-[(S,S)-3,5-bis(1-methoxyethyl)-1,2,4-triazol-4-yl]-2,2-dimethoxyethylimine and 1.3 g of magnesium bromide are introduced under nitrogen into 60 ml of dichloromethane in a 100 ml three-necked flask equipped with a magnetic stirrer and a reflux condenser. The reaction medium is stirred at ambient temperature for 20 min and then cooled to 0° C. 0.018 mol of ethylmagnesium bromide prepared beforehand in diethyl ether (15 ml) is subsequently added dropwise over approximately 1 h. At the end of this addition, the reaction medium is kept stirred at 0° C. for 3 hours. The reaction medium is poured onto a saturated aqueous ammonium chloride solution. The aqueous phase is extracted with 5 times 30 ml of CH$_2$Cl$_2$. The organic phases are combined and the resulting organic phase is dried over anhydrous magnesium sulphate before being concentrated. 1.09 g of the mixture of the diastereoisomers are obtained.

The mixture of the diastereoisomers is chromatographed (m=0.63 g) on a 10 mm×250 mm column in which the stationary phase is a Chiralpak AD® (amylose tris(3,5-dimethylphenylcarbamate)) under the following conditions:
Ambient temperature
Flow rate of 4 ml/min
Mobile phase hexane/isopropanol (60/40)
Separation measured by absorption at 210 nm 4-[(S)-1-Ethyl-2,2-dimethoxyethylamino]-(S,S)-3,5-bis(1-methoxyethyl)-1,2,4-triazole

[α]$^{25}_D$=+25.420 (c=0.676, CHCl$_3$) M.p.=74° C. $^1$H NMR (CDCl$_3$): δ 0.89 (t, J=7.4 Hz, 3H, CH$_3$), 1.43 (m, 2H, CH$_2$), 1.59 (d, J=6.6 Hz, 6H, CH$_3$), 3.28 (s, 6H, CH$_3$), 3.293 (s, 6H, CH$_3$), 3.37 (m, 1H, CH), 4.19 (d, J=4.8 Hz, 1H, CH), 4.75 (q, J=6.6 Hz, 2H, CH), 5.55 (d, J=4.8 Hz, 1H, NH) ppm. $^{13}$C NMR (CDCl$_3$): δ 10.55 (CH$_3$), 16.83 (CH$_3$), 21.78 (CH$_2$), 54.76 (CH$_3$), 54.95 (CH$_3$), 56.02 (CH$_3$), 62.27 (CH), 69.41 (CH), 105.43 (CH), 154.77 (N—C=N) ppm.

4-[(R)-1-Ethyl-2,2-dimethoxyethylamino]-(S,S)-3,5-bis(1-methoxyethyl)-1,2,4-triazole $[\alpha]^{25}_D$=−13.570 (c=1.024, CHCl$_3$) M.p.=67–68° C. $^1$H NMR (CDCl$_3$): δ 0.82 (t, J=7.5 Hz, 3H, CH$_3$), 1.4 (m, 2H, CH$_2$), 1.61 (d, J=6.8 Hz, 6H, CH$_3$), 3.26 (s, 6H, CH$_3$), 3.35 and 3.37 (s, 6H, CH$_3$), 3.39 (m, 1H, CH), 4.3 (d, J=5.2 Hz, 1H, CH), 4.75 (q, J=6.8 Hz, 2H, CH), 5.33 (d, J=4.2 Hz, 1H, NH) ppm. $^{13}$C NMR (CDCl$_3$): δ 10.12 (CH$_3$), 17.27 (CH$_3$), 21.50 (CH$_2$), 54.87 (CH$_3$), 54.96 (CH$_3$), 55.54 (CH$_3$), 62.44 (CH), 69.19 (CH), 104.84 (CH), 154.97 (N—C=N) ppm.

EXAMPLE 6

4-[1-Phenyl-2,2-dimethoxyethylamino]-(S,S)-3,5-bis(1-methoxyethyl)-1,2,4-triazole (Treatment of a Compound of Formula (IV) with an Organometallic Compound)

4.3 g of cerium chloride are introduced under nitrogen into 50 ml of THF in a 100 ml three-necked flask equipped with a magnetic stirrer and a reflux condenser. This mixture is stirred at ambient temperature for 2 h and then under ultrasound for a further 1 h. After halting the ultrasound treatment, the reaction medium is brought to a temperature of −78° C. (ethanol/liquid nitrogen bath) and then a phenylmagnesium bromide solution (0.0175 mol) is added over approximately 15 min. The medium is then maintained at a temperature of −78° C. for 2 h with stirring. The temperature of the reaction medium is subsequently brought to a temperature of −100° C. 1 g (0.0035 mol) of N-[(S,S)-3,5-bis(1-methoxyethyl)-1,2,4-triazol-4-yl]-2,2-dimethoxyethylimine, in solution in 10 ml of THF, is added at this temperature over 1 h. The reaction medium is then kept stirred at −100° C. for 2 h and then is brought back to ambient temperature overnight. The reaction medium is poured onto a saturated aqueous NaHCO$_3$ solution (50 ml). The aqueous phase is extracted several times with ethyl acetate and then the organic phases are combined. The resulting organic phase is dried over anhydrous magnesium sulphate before being concentrated. 1.60 g of the expected compound are obtained.

$^1$H NMR (CDCl$_3$): Mixture of diastereoisomers δ 1.33 or 1.5 (d, J=6.6 Hz, 6H, CH$_3$), 3.21 (s, 6H, CH$_3$), 3.26 (s, 3H, CH$_3$), 3.46 (s, 3H, CH$_3$), 4.28 or 4.5 (q, J=6.6 Hz, 2H, CH), 4.52 (m, 1H, CH), 4.71 (d, J=6.2 Hz, 1H, CH), 5.78 (d, J=4.6 Hz, 1H, NH), 7.13–7.28 (m, 5H, H$_{aromatic}$) ppm. $^{13}$C NMR (CDCl$_3$): Mixture of diastereoisomers δ 16.47 and 18.00 (CH$_3$), 54.43 and 55.88 (CH$_3$), 67.102 and 67.35 (CH), 68.21 and 70.47 (CH), 105.30 and 105.50 (CH), 128.78–129.26 (CH$_{aromatic}$), 136.07 (C$_{aromatic}$), 154.28 and 155.10 (N—C=N) ppm.

EXAMPLE 7

4-[(R and S)-1-Ethyl-2,2-dimethoxyethylamino]-(S,S)-3,5-bis(1-ethoxyethyl)-1,2,4-triazole (Treatment of a Compound of Formula (IV) with an Organometallic Compound)

1 g of N-[(S,S)-3,5-bis(1-ethoxyethyl)-1,2,4-triazol-4-yl]-2,2-dimethoxyethylimine is introduced under nitrogen into 60 ml of dichloromethane in a 100 ml three-necked flask equipped with a magnetic stirrer and a reflux condenser. The temperature is subsequently brought to 0° C. and then 0.018 mol of ethylmagnesium bromide prepared beforehand in diethyl ether (15 ml) is added dropwise over approximately one hour. At the end of this addition, the reaction medium is kept stirred at 0° C. for three hours. The reaction medium is poured onto a saturated aqueous ammonium chloride solution. The aqueous phase is extracted with 5 times 30 ml of CH$_2$Cl$_2$ and then the organic phases are combined. The resulting organic phase is dried over anhydrous magnesium sulphate before being concentrated. 1.00 g of the mixture of the diastereoisomers is obtained.

The mixture of the diastereoisomers is chromatographed (m=0.45 g) on a 10 mm×250 mm column in which the stationary phase is a Chiralpak AD® (amylose tris(3,5-dimethylphenylcarbamate)) under the following conditions:

Ambient temperature

Flow rate of 4 ml/min

Mobile phase hexane/isopropanol (80/20)

Separation measured by absorption at 210 nm

4-[(R)-1-Ethyl-2,2-dimethoxyethylamino]-(S,S)-3,5-bis(1-ethoxyethyl)-1,2,4-triazole $[\alpha]^{25}_D$+7.85° (c=0.764, CHCl$_3$) M.p.=94° C. $^1$H NMR (CDCl$_3$): δ 0.91 (t, J=7.5 Hz, 3H, CH$_3$), 1.22 (t, J=7 Hz, 6H, CH$_3$), 1.5 (m, 2H, CH$_2$), 1.72 (d, J=6.8 Hz, 6H, CH$_3$), 3.48 (s, 3H, CH$_3$), 3.49 (s, 3H, CH$_3$), 3.5 (m, 5H, CH$_2$ and CH), 4.42 (d, J=5 Hz, 1H, CH), 4.91 (q, J=6.8 Hz, 2H, CH), 5.58 (d, J=5 Hz, 1H, NH) ppm. $^{13}$C NMR (CDCl$_3$): δ 15.36 (CH$_3$), 17.91 (CH$_3$), 21.47 (CH$_2$), 55.05 (CH$_3$), 55.81 (CH$_3$), 62.65 (CH), 62.97 (CH$_2$), 68.06 (CH), 105.01 (CH), 155.10 (N—C=N) ppm.

4-[(S)-1-Ethyl-2,2-dimethoxyethylamino]-(S,S)-3,5-bis(1-ethoxyethyl)-1,2,4-triazole $[\alpha]^{25}_D$=+45.42° (c=1.114, CHCl$_3$) M.p.=88° C. $^1$H NMR (CDCl$_3$): δ 0.85 (t, J=7.5 Hz, 3H, CH$_3$), 1.14 (t, J=7 Hz, 6H, CH$_3$), 1.45 (m, 2H, CH$_2$), 1.60 (d, J=6.8 Hz, 6H, CH$_3$), 3.31 (s, 3H, CH$_3$), 3.37 (s, 3H, CH$_3$), 3.45 (m, 5H, CH$_2$ and CH), 4.20 (d, J=5 Hz, 1H, CH), 4.81 (q, J=6.8 Hz, 2H, CH), 5.59 (d, J=5 Hz, 1H, NH) ppm. $^{13}$C NMR (CDCl$_3$): δ 15.41 (CH$_3$), 17.53 (CH$_3$), 21.15 (CH$_2$), 54.73 (CH$_3$), 56.07 (CH$_3$), 62.60 (CH), 63.06 (CH$_2$), 68.36 (CH), 105.44 (CH), 155.05 (N—C=N) ppm.

EXAMPLE 8

4-[1-Ethyl-2,2-dimethoxyethylamino]-(S,S)-3,5-bis(1-(2-methoxyethoxy)ethyl)-1,2,4-triazole (Treatment of a Compound of Formula (IV) with an Organometallic Compound)

0.7 g of N-[(S,S)-3,5-bis(1-(2-methoxyethoxy)ethyl)-1,2,4-triazol-4-yl]-2,2-dimethoxyethylimine is introduced under nitrogen into 40 ml of dichloromethane in a 100 ml three-necked flask equipped with a magnetic stirrer and a reflux condenser. The temperature is subsequently brought to 0° C. and then 0.093 mol of ethylmagnesium bromide prepared beforehand in diethyl ether (7 ml) is added dropwise over approximately one hour. The reaction medium is subsequently kept stirred at 0° C. for three hours. The reaction medium is poured onto a saturated aqueous ammonium chloride solution. The aqueous phase is extracted with 5 times 15 ml of CH$_2$Cl$_2$ and the organic phases are combined. The resulting organic phase is dried over anhydrous magnesium sulphate before being concentrated. 0.80 g of the expected compound is obtained.

Gas chromatography retention times:

$t_R$=18.42 min with the following conditions:

detection: flame ionization detector capillary column: CP-SIL 5 (length 30 m; thickness 0.25 µm; diameter 0.25 mm), manufactured by Chrompack injector temperature: 300° C.

detector temperature: 300° C.

column temperature: 180° C. to 280° C. (8° C./min), then 20 min at 280° C., and $t_R$=27.13 min with the following conditions:

detection: flame ionization detector capillary column: CP-SIL 5CB-MF (length 30 m; thickness 0.25 µm; diameter 0.32 mm), manufactured by Chrompack® injector temperature: 250° C.

detector temperature: 300° C.

column temperature: 170° C. for 5 min, then 170° C. to 280° C. (3° C./min), then 30 min at 280° C.

EI MS m/z (relative intensity, %): 329 (M-75, 39), 253 (34), 212 (10), 177 (24), 122 (27), 75 (100), 59 (36), 45 (57): analysis by Mass Spectrometry coupled to Gas Chromatography (Varian 3500 GC device coupled to a Unicam Automass 150 mass spectrometry detector) under the following conditions:

Capillary column: BPX35 (length 30 m; thickness 0.25 µm; diameter 0.25 mm), manufactured by SGE Injector temperature: 300° C.

Detector temperature: 300° C.

Column temperature: 120° C. to 220° C. (10° C./min), then 5 min at 220° C., then 220° C. to 280° C. (10° C./min).

EXAMPLE 9

4-[1-Ethylbutylamino]-(S,S)-3,5-bis(1-methoxyethyl)-1,2,4-triazole (Treatment of a Compound of Formula (IV) with an Organometallic Compound)

25 ml of THF are introduced under nitrogen into a 100 ml three-necked flask equipped with a magnetic stirrer and a reflux condenser. The ethylmagnesium bromide solution prepared beforehand in diethyl ether is added. The reaction medium is brought to a temperature of 0° C. An N-[(S,S)-3,5-bis(1-methoxyethyl)-1,2,4-triazol-4-yl]butylimine solution (0.7 g, 5 ml THF) is added over approximately one hour. At the end of this addition, the temperature of the medium is kept at 0° C. for 3 h. The reaction medium is poured onto a saturated aqueous ammonium chloride solution. The aqueous phase is extracted several times with dichloromethane and the organic phases are combined. The resulting organic phase is dried over anhydrous magnesium sulphate before being concentrated. 0.85 g of the expected compound is obtained.

$^1$H NMR (CDCl$_3$): δ 0.85 (m, 6H, CH$_3$), 1.3 (m, 6H, CH$_2$), 1.58 (d, J=6.6 Hz, 6H, CH$_3$), 3.2 (m, 1H, CH), 3.28 (s, 6H, CH$_3$), 4.7 (q, J=6.6 Hz, 2H, CH), 5.07 (d, J=3.8 Hz, 1H, NH) ppm. $^{13}$C NMR (CDCl$_3$): δ 9.63 (CH$_3$), 14.25 (CH$_3$), 17.52 (CH$_3$), 18.64 (CH$_2$), 21.14 (CH$_2$), 33.87 (CH$_2$), 55.28 (CH$_3$), 61.41 (CH), 70.03 (CH), 155.06 (N—C=N) ppm.

EXAMPLE 10

4-[1-Ethylisobutylamino]-(S,S)-3,5-bis(1-methoxyethyl)-1,2,4-triazole (Treatment of a Compound of Formula (IV) with an Organometallic Compound)

25 ml of THF are introduced under nitrogen into a 100 ml three-necked flask equipped with a magnetic stirrer and a reflux condenser. The ethylmagnesium bromide solution prepared beforehand in diethyl ether is added. The reaction medium is brought to a temperature of 0° C. and then an N-[(S,S)-3,5-bis(1-methoxyethyl)-1,2,4-triazol-4-yl]isobutylimine solution (0.5 g, 5 ml THF) is added over approximately one hour. At the end of this addition, the temperature of the medium is kept at 0° C. for 3 h. The reaction medium is poured onto a saturated aqueous ammonium chloride solution. The aqueous phase is extracted several times with dichloromethane and the organic phases are combined. The resulting organic phase is dried over anhydrous magnesium sulphate before being concentrated.

Crude Yd=100%; m=0.60 g. $^1$H NMR (CDCl$_3$): δ 0.75 (t, J=7.4 Hz, 3H, CH$_3$), 0.84 (d, J=6.88 Hz, 3H, CH$_3$), 0.93 (d, J=6.9 Hz, 3H, CH$_3$), 1.4 (m, 2H, CH$_2$), 1.55 (d, J=6.6 Hz, 6H, CH$_3$), 1.8 (m, 1H, CH), 3.05 (m, 1H, CH), 3.25 (s, 6H, CH$_3$), 4.68 (q, J=6.6 Hz, 2H, CH), 5.06 (d, J=3.4 Hz, 1H, NH) ppm. $^{13}$C NMR (CDCl$_3$): δ 10.75 (CH$_3$), 16.81 (CH$_3$), 17.26 (CH$_3$), 18.04 (CH$_3$), 20.80 (CH$_2$), 28.18 (CH), 55.13 (CH$_3$), 65.71 (CH), 69.74 (CH), 155.19 (N—C=N) ppm.

EXAMPLE 11

4-[1-Phenylpropylamino]-(S,S)-3,5-bis(1-methoxyethyl)-1,2,4-triazole (Treatment of a Compound of Formula (IV) with an Organometallic Compound)

4.05 ml of a 3M solution of ethylmagnesium bromide in diethyl ether are introduced under nitrogen into 35 ml of THF in a 100 ml three-necked flask equipped with a magnetic stirrer and a reflux condenser. The reaction medium is brought to a temperature of 0° C. and then an N-[(S,S)-3,5-bis(1-methoxyethyl)-1,2,4-triazol-4-yl]benzylimine solution (0.7 g, 5 ml THF) is added over approximately one hour. At the end of this addition, the temperature of the medium is kept at 0° C. for 3 h. The reaction medium is poured onto a saturated aqueous ammonium chloride solution. The aqueous phase is extracted several times with dichloromethane and the organic phases are combined. The resulting organic phase is dried over anhydrous magnesium sulphate before being concentrated. 0.90 g of the expected compound is obtained.

Gas chromatography retention times:

$t_R$=27.27 min (S,S,S)

$t_R$=27.69 min (S,S,R), with the following conditions:

detection: flame ionization detector capillary column: CP-SIL 5 (length 30 m; thickness 0.25 µm; diameter 0.25 mm), manufactured by Chrompack injector temperature: 300° C.

detector temperature: 300° C.

column temperature: 120° C. to 230° C. (7° C./min), then 230° C. to 280° C. (3° C./min), then 10 min at 280° C.

EI MS m/z (relative intensity, %): 318 (M, 1), 289 (M−29, 19), 257 (46), 225 (14), 170 (43), 134 (45), 122 (41), 91 (100), 59 (57): analysis by Mass Spectrometry coupled to Gas Chromatography (Varian 3500 GC device coupled to a Unicam Automass 150 mass spectrometry detector) under the following conditions:

capillary column: BPX35 (length 30 m; thickness 0.25 μm; diameter 0.25 mm), manufactured by SGE
injector temperature: 300° C.
detector temperature: 300° C.
column temperature: 120° C. to 220° C. (10° C./min), then 5 min at 220° C., then 220° C. to 280° C. (10° C./min).

EXAMPLE 12

N-[(S,S)-3,5-Bis(1-methoxyethyl)-1,2,4-triazol-4-yl]-(2,2-dimethoxyethylimine (Treatment of a Compound of Formula (V) with an Aldehyde)

60 ml of 1,2-dichloroethane, 7.8 g of (S,S)-4-amino-3,5-bis(1-methoxyethyl)-1,2,4-triazole and 8.1 g of a 60% aqueous dimethoxyethanal solution are introduced into a 100 ml three-necked flask equipped with a magnetic stirrer and a heavy-phase Dean and Stark apparatus surmounted by a reflux condenser and a dropping funnel. The reaction medium is brought to reflux to remove the water by azeotropic distillation. 0.15 g of para-toluenesulphonic acid (PTSA) is then introduced and the reaction medium is brought to reflux for 3 h. After returning to ambient temperature, the medium is neutralized by addition of triethylamine and then concentrated. The residue is taken up in heptane under hot conditions, filtered and dried. 10.3 g of the expected product are obtained.

M.p.=96–100° C. $[\alpha]^{25}_D$=–72.290 (c=1.256, CHCl$_3$) $^1$H NMR (CDCl$_3$): δ 1.62 (d, J=6.7 Hz, 6H, CH$_3$), 3.32 (s, 6H, CH$_3$), 3.52 (2 adhering s, 6H, CH$_3$), 4.7 (q, J=6.8 Hz, 2H, CH), 4.97 (d, J=5.4 Hz, 1H, CH), 8.17 (d, J=5.4 Hz, 1H, CH) ppm. $^{13}$C NMR (CDCl$_3$): δ 17.21 (CH$_3$), 54.33 (CH$_3$), 54.56 (CH$_3$), 55.85 (CH$_3$), 70.31 (CH), 101.75 (CH), 151.90 (N—C=N), 165.69 (CH) ppm.

EXAMPLE 13

N-[(S,S)-3,5-Bis(1-ethoxyethyl)-1,2,4-triazol-4-yl]-2,2-dimethoxyethylimine (Treatment of a Compound of Formula (V) with an Aldehyde)

The compound is prepared as in Example 12, except that (S,S)-4-amino-3,5-bis(1-ethoxyethyl)-1,2,4-triazole is used. 5.2 g of crude product (oil) are obtained.

$[\alpha]^{25}_D$=–65.750 (c=1.142, CHCl$_3$) $^1$H NMR (CDCl$_3$): δ 1.02 (t, J=7 Hz, 6H, CH$_3$), 1.45 (d, J=6.7 Hz, 6H, CH$_3$), 3.25 (m, 4H, CH$_2$), 3.36 (s, 6H, CH$_3$), 4.63 (q, J=6.8 Hz, 2H, CH), 4.81 (d, J=5.4 Hz, 1H, CH), 8.08 (d, J=5.4 Hz, 1H, CH) ppm. $^{13}$C NMR (CDCl$_3$): δ 14.921 (CH$_3$), 17.476 (CH$_3$), 54.067 (CH$_3$), 54.335 (CH$_3$), 63.749 (CH$_2$), 68.641 (CH), 101.561 (CH), 152.066 (N—C=N), 165.574 (CH) ppm.

EXAMPLE 14

N-[(S,S)-3,5-Bis(1-(2-methoxyethoxy)ethyl)-1,2,4-triazol-4-yl]-2,2-dimethoxyethylimine (Treatment of a Compound of Formula (V) with an Aldehyde)

The compound is prepared as in Example 12, except that (S,S)-4-amino-3,5-bis(1-(2-methoxyethoxy)ethyl)-1,2,4-triazole is used. 1.8 g of crude product (oil) are obtained.

$^1$H NMR (CDCl$_3$): δ 1.56 (d, J=6.8 Hz, 6H, CH$_3$), 3.21 (s, 6H, CH$_3$), 3.45 (s, 6H, CH$_3$), 3.50 (m, 8H, CH$_2$), 4.77 (q, J=6.8 Hz, 2H, CH), 4.94 (d, J=4.8 Hz, 1H, CH), 8.33 (d, J=5 Hz, 1H, CH) ppm. $^{13}$C NMR (CDCl$_3$): δ 17.367 (CH$_3$), 53.816 (CH$_3$), 54.038 (CH$_3$), 58.562 (CH$_3$), 67.102 (CH$_2$), 69.016 (CH), 71.415 (CH$_2$), 101.272 (CH), 151.769 (N—C=N), 167.890 (CH) ppm.

EXAMPLE 15

N-[(S,S)-3,5-Bis(1-methoxyethyl)-1,2,4-triazol-4-yl]butylimine (Treatment of a Compound of Formula (V) with an Aldehyde)

0.54 g of butyraldehyde and 1.5 g of (S,S)-4-amino-3,5-bis(1-methoxyethyl)-1,2,4-triazole are introduced into toluene (20 ml) in the presence of a catalytic amount (0.02 mol. eq.) of para-toluenesulphonic acid in a 100 ml round-bottomed flask equipped with a magnetic stirrer and a Dean and Stark apparatus surmounted by a reflux condenser. The reaction medium is heated at reflux for 3 h. After returning to ambient temperature and neutralizing by addition of triethylamine, the medium is concentrated. 1.80 g of the expected compound (oily product) are obtained.

$^1$H NMR (CDCl$_3$): δ 1.01 (t, J=7.4 Hz, 3H, CH$_3$), 1.53 (d, J=6.8 Hz, 6H, CH$_3$), 1.7 (m, 2H, CH$_2$), 2.49 (m, 2H, CH$_2$), 3.23 (s, 6H, CH$_3$), 4.6 (q, J=6.8 Hz, 2H, CH), 8.07 (t, J=5.4 Hz, 1H, CH) ppm. $^{13}$C NMR (CDCl$_3$): δ 13.56 (CH$_3$), 17.14 (CH$_3$), 18.74 (CH$_2$), 35.00 (CH$_2$), 55.66 (CH$_3$), 70.22 (CH), 151.35 (N—C=N), 175.08 (CH) ppm.

EXAMPLE 16

N-[(S,S)-3,5-Bis(1-methoxyethyl)-1,2,4-triazol-4-yl]isobutylimine (Treatment of a Compound of Formula (V) with an Aldehyde)

0.36 g of isobutyraldehyde and 1 g of (S,S)-4-amino-3,5-bis(1-methoxyethyl)-1,2,4-triazole are introduced into toluene (10 ml) in the presence of a catalytic amount (0.02 mol. eq.) of para-toluenesulphonic acid in a 100 ml round-bottomed flask equipped with a magnetic stirrer and a Dean and Stark apparatus surmounted by a reflux condenser. The reaction medium is heated at reflux for 3 h. After returning to ambient temperature and neutralizing by addition of triethylamine, the medium is concentrated. 1.20 g of the expected compound (oily product) are obtained.

$^1$H NMR (CDCl$_3$): δ 1.12 (d, J=6.85 Hz, 6H, CH$_3$), 1.46 (d, J=6.75 Hz, 6H, CH$_3$), 2.72 (m, 1H, CH), 3.16 (s, 6H, CH$_3$), 4.53 (q, J=6.75 Hz, 2H, CH), 7.90 (d, J=5.3 Hz, 1H, CH) ppm. $^{13}$C NMR (CDCl$_3$): δ 17.17 (CH$_3$), 18.67 (CH$_3$), 32.48 (CH), 55.85 (CH$_3$), 70.34 (CH), 151.44 (N—C=N), 179.57 (CH) ppm.

EXAMPLE 17

N-[(S,S)-3,5-Bis(1-methoxyethyl)-1,2,4-triazol-4-yl]-1-(ethoxycarbonyl)methylimine (Treatment of a Compound of Formula (V) with an Aldehyde)

0.64 g of a 50% solution of ethyl glyoxylate in toluene and 0.6 g of (S,S)-4-amino-3,5-bis(1-methoxyethyl)-1,2,4-triazole are introduced into toluene (10 ml) in the presence of a catalytic amount (0.02 mol. eq.) of para-toluenesulphonic acid in a 100 ml round-bottomed flask equipped with a magnetic stirrer and a Dean and Stark apparatus surmounted by a reflux condenser. The reaction medium is heated at reflux for 3 h. After returning to ambient temperature, the medium is concentrated. 0.80 g of the expected compound (oily product) is obtained.

$^1$H NMR (CDCl$_3$): δ 1.23 (t, J=7.12 Hz, 3H, CH$_3$), 1.45 (d, J=6.75 Hz, 6H, CH$_3$), 3.18 (s, 6H, CH$_3$), 4.25 (q, J=7.12

Hz, 2H, CH$_2$), 4.63 (q, J=6.75 Hz, 2H, CH), 8.32 (s, 1H, CH) ppm. $^{13}$C NMR (CDCl$_3$): δ 13.915 (CH$_3$), 16.979 (CH$_3$), 55.983 (CH$_3$), 62.485 (CH$_2$), 70.058 (CH), 152.305 (N—C=N), 152.761 (COOR), 161.425 (CH) ppm.

EXAMPLE 18

N-[(S,S)-3,5-Bis(1-methoxyethyl)-1,2,4-triazol-4-yl] benzylimine (Treatment of a Compound of Formula (V) with an Aldehyde)

1.8 g of benzaldehyde and 3.4 g of (S,S)-4-amino-3,5-bis (1-methoxyethyl)-1,2,4-triazole are introduced into toluene (60 ml) in the presence of a catalytic amount (0.02 mol. eq.) of para-toluenesulphonic acid in a 100 ml round-bottomed flask equipped with a magnetic stirrer and a Dean and Stark apparatus surmounted by a reflux condenser. The reaction medium is heated at reflux for 3 h. After returning to ambient temperature and neutralizing by addition of triethylamine, the mixture is concentrated. The residue is stirred in hexane in order to remove the traces of benzaldehyde. 4.20 g of the expected compound (oily product) is obtained.

$^1$H NMR (CDCl$_3$): δ 1.65 (d, J=6.75 Hz, 6H, CH$_3$), 3.36 (s, 6H, CH$_3$), 4.77 (q, J=6.8 Hz, 2H, CH), 7.50–7.62 (m, 3H, H$_{aromatic}$), 7.87–7.92 (m, 2H, H$_{aromatic}$), 8.82 (s, 1H, CH) ppm. $^{13}$C NMR (CDCl$_3$): δ 17.35 (CH$_3$), 56.09 (CH$_3$), 70.47 (CH), 129.10–133.09 (C$_{aromatic}$), 151.98 (N—C=N), 167.31 (CH) ppm.

EXAMPLE 19

N,N'-Bis[(S,S)-3,5-bis(1-methoxyethyl)-1,2,4-triazol-4-yl]methylimine (Treatment of a Compound of Formula (V) with an Aldehyde)

1 g of (S,S)-4-amino-3,5-bis(1-methoxyethyl)-1,2,4-triazole and 0.36 g of a 40% aqueous glyoxal solution are introduced into a 100 ml three-necked flask equipped with a magnetic stirrer and a heavy-phase Dean and Stark apparatus surmounted by a reflux condenser. After stirring for 2 h, 15 ml of 1,2-dichloroethane are added. The mixture is left stirring for 1 h, then a catalytic amount of para-toluenesulphonic acid (0.02 mol. eq.) is introduced and the reaction medium is brought to reflux for 3 h. After returning to ambient temperature, the medium is concentrated. A coloured oil is obtained.

$^1$H NMR (CDCl$_3$): δ 1.59 (d, J=6.6 Hz, 12H, CH$_3$), 3.29 (s, 12H, CH$_3$), 4.75 (q, J=6.7 Hz, 4H, CH), 8.85 (s, 2H, CH) ppm. $^{13}$C NMR (CDCl$_3$): δ 17.10 (CH$_3$), 55.91 (CH$_3$), 70.29 (CH), 152.46 (N—C=N), 159.22 (CH) ppm.

EXAMPLE 20

N-[(S,S)-3,5-Bis(1-methoxyethyl)-1,2,4-triazol-4-yl]-1-methylbenzylimine (Treatment of a Compound of Formula (V) with a Ketone)

0.6 g of acetophenone and 1 g of (S,S)-4-amino-3,5-bis (1-methoxyethyl)-1,2,4-triazole are introduced into ortho-xylene (10 ml) in the presence of a catalytic amount (0.02 mol. eq.) of para-toluenesulphonic acid in a 100 ml round-bottomed flask equipped with a magnetic stirrer and a Dean and Stark apparatus surmounted by a reflux condenser. The reaction medium is heated at reflux for 40 h (change monitored by Gas Chromatography (GC)). After returning to ambient temperature, the medium is neutralized with triethylamine and concentrated. The residue is taken up several times in hexane under hot conditions and the supernatant phase is separated. A solid is formed in the separated phase. 1.00 g of the expected compound is obtained.

M.p.=102° C. $^1$H NMR (CDCl$_3$): (signals of the triazole ring in the unresolved peak) δ 1.60 (m, 6H, CH$_3$), 2.25 (s, 3H, CH$_3$), 4.6 (m, 2H, CH), 7.52–7.61 (m, 3H, H$_{aromatic}$), 7.96–8.02 (m, 2H, H$_{aromatic}$) ppm. $^{13}$C NMR (CDCl$_3$): δ 17.05 (CH$_3$), 17.468 (CH$_3$), 55–56 (CH$_3$), 70–71 (CH), 127.61–135.61 (C$_{aromatic}$), 151 (N—C=N), 179.99 (C$_{quaternary}$) ppm.

EXAMPLE 21

N-[(S,S)-3,5-Bis(1-methoxyethyl)-1,2,4-triazol-4-yl]-2,2-dimethoxy-1-methylethylimine (Treatment of a Compound of Formula (V) with a Ketone)

0.79 g of pyruvaldehyde dimethyl acetal and 1 g of (S,S)-4-amino-3,5-bis(1-methoxyethyl)-1,2,4-triazole are introduced into toluene (15 ml) in the presence of a catalytic amount (0.02 mol. eq.) of para-toluenesulphonic acid in a 100 ml round-bottomed flask equipped with a magnetic stirrer and a Dean and Stark apparatus surmounted by a reflux condenser. The reaction medium is heated at reflux for 6 h. After returning to ambient temperature, the medium is concentrated. 1.20 g of the expected compound (oily product) are obtained.

$^1$H NMR (CDCl$_3$): δ 1.38 (d, J=6.65 Hz, 6H, CH$_3$), 1.64 (s, 3H, CH$_3$), 3.08 (s, 6H, CH$_3$), 3.33 (s, 3H, CH$_3$), 3.36 (s, 3H, CH$_3$), 4.31 (m, 2H, CH), 4.63 (s, 1H, CH) ppm. $^{13}$C NMR (CDCl$_3$): δ 13.598 (CH$_3$), 16.6–17.4 (CH$_3$), 55.211 (CH$_3$), 55.617 (CH$_3$), 56.180 (CH$_3$), 70.345 (CH), 104.994 (CH), 150.648 (N—C=N), 182.991 (C$_{quaternary}$) ppm.

EXAMPLE 22

4-[1-Phenylethylamino]-(S,S)-3,5-bis(1-methoxyethyl)-1,2,4-triazole (Catalytic Hydrogenation of a Compound of Formula (IV))

0.3 g of N-[(S,S)-3,5-bis(1-methoxyethyl)-1,2,4-triazol-4-yl]benzylimine and 1.5 g of a 50% solution of Raney nickel in water are introduced into 100 ml of ethanol in an autoclave. The medium is placed under 10 bar of hydrogen and is heated at 100° C. for approximately 24 h. The reaction medium is filtered through celite and concentrated. 0.27 g of the expected compound is obtained.

EXAMPLE 23

4-[1-Phenylethylamino]-(S,S)-3,5-bis(1-methoxyethyl)-1,2,4-triazole (Reduction of a Compound of Formula (IV))

0.3 g of N-[(S,S)-3,5-bis(1-methoxyethyl)-1,2,4-triazol-4-yl]-1-methylbenzylimine is introduced into 5 ml of THF in a 100 ml round-bottomed flask. One molar equivalent of lithium borohydride as a 2M solution in tetrahydrofuran (0.98 ml) is added to this solution with stirring at ambient temperature over approximately 1.5 h. After refluxing for 2 hours, this medium is left stirring at ambient temperature for 16 hours. A 20% sodium hydroxide solution (20 ml) is added, along with 30 ml of dichloromethane. After separating the phases by settling, the aqueous phase is extracted several times with dichloromethane. The organic phases are combined and the resulting organic phase is dried and concentrated. 0.30 g of the expected compound is obtained.

GC retention times:
$t_R$=25.98 min (S,S,S)
$t_R$=26.54 min (S,S,R), with the following conditions:
detection: flame ionization detector
capillary column: CP-SIL 5 (length 30 m; thickness 0.25 μm; diameter 0.25 mm), manufactured by Chrompack
injector temperature: 300° C.
detector temperature: 300° C.
column temperature: 120° C. to 230° C. (7° C./min), then 230° C. to 280° C. (3° C./min), then 10 min at 280° C.
EI MS m/z (relative intensity, %): 318 (M, 1), 289 (M–29, 19), 257 (46), 225 (14), 170 (43), 134 (45), 122 (41), 91 (100), 59 (57): analysis by Mass Spectrometry coupled to Gas Chromatography (Varian 3500 GC device coupled to a Unicam Automass 150 mass spectrometry detector) under the following conditions:
capillary column: BPX35 (length 30 m; thickness 0.25 μm; diameter 0.25 mm), manufactured by SGE
injector temperature: 300° C.
detector temperature: 300° C.
column temperature: 120° C. to 220° C. (10° C./min), then 5 min at 220° C., then 220° C. to 280° C. (10° C./min).

EXAMPLE 24

Preparation of the starting (S,S)-4-amino-3,5-bis(1-methoxyethyl)-1,2,4-triazole of Example 12

2.3 g of 60% sodium hydride coated in a mineral oil are introduced into a 250 ml three-necked flask. The sodium hydride is suspended in 10 ml of anhydrous hexane and is washed 3 times with 10 ml of anhydrous hexane. After the final washing, the sodium hydride is suspended in 60 ml of anhydrous dimethylformamide (DMF). The round-bottomed flask is then equipped with a reflux condenser, supplied with a bubbler, and with a magnetic stirrer. The temperature of the reaction medium is brought to 0° C. and then a solution of (S,S)-4-amino-3,5-bis(1-hydroxyethyl)-1,2,4-triazole, prepared according to the reference J. Heterocycles, 1987, 26, 989–1000, in 35 ml of DMF is added dropwise over approximately 15 min. After gas has ceased being evolved (approximately 30 min after the end of the addition), a solution of methyl tosylate (0.058 mol) in 25 ml of DMF is added dropwise. The temperature is maintained at 0° C. for a further 30 min after the end of the addition. The medium is allowed to slowly return to ambient temperature with stirring and concentrated, and the residue is extracted with 5 times 50 ml of a 50/50 (v/v) AcOEt/CHCl$_3$ mixture. The extraction phase is concentrated. The oil obtained is purified by addition of 0.029 mol of hydrochloric acid as a 10% aqueous solution and then extraction is carried out with 6 times 10 ml of CH$_2$Cl$_2$. 0.029 mol of sodium hydroxide as a 10% aqueous solution is then added to the aqueous phase obtained and then continuous liquid-liquid extraction is carried out with CH$_2$Cl$_2$. The organic phase obtained is dried over magnesium sulphate and concentrated. 5.15 g of the expected compound are obtained (oily product which sets solid).

$^1$H NMR (CDCl$_3$): δ 1.33 (d, J=6.7 Hz, 6H, CH$_3$), 3.05 (s, 6H, OCH$_3$), 4.53 (q, J=6.7 Hz, 2H, CH), 5.35 (s, 2H, NH$_2$) ppm. $^{13}$C NMR (CDCl$_3$): δ 17.15 (CH$_3$), 55.85 (CH$_3$), 69.72 (CH), 154.23 (N—C═N) ppm.

EXAMPLE 25

Preparation of the starting (S,S)-4-amino-3,5-bis(1-ethoxyethyl)-1,2,4-triazole of Example 13

The compound is prepared as in Example 24 but using ethyl tosylate. A coloured oil is obtained.

$^1$H NMR (CDCl$_3$): δ 1.06 (t, J=7 Hz, 3H, CH$_3$), 1.50 (d, J=6.7 Hz, 6H, CH$_3$), 3.4 (m, 4H, CH$_2$), 4.70 (q, J=6.7 Hz, 2H, CH), 5.23 (s, 2H, NH$_2$) ppm. $^{13}$C NMR (CDCl$_3$): δ 15.30 (CH$_3$), 18.20 (CH$_3$), 64.30 (CH$_2$), 69.30 (CH), 153.90 (N—C═N) ppm.

EXAMPLE 26

[Hexyl-3,4-diamino]-4,4'-bis[(S,S)-3,5-bis(1-methoxyethyl)-1,2,4-triazole]

0.6 g of N,N'-bis[(S,S)-3,5-bis(1-methoxyethyl)-1,2,4-triazol-4-yl]methylimine is introduced under nitrogen into 25 ml of CH$_2$Cl$_2$ in a 100 ml three-necked flask equipped with a magnetic stirrer and a reflux condenser. The reaction medium is brought to a temperature of between –10° C. and 0° C. and then the solution of ethylmagnesium bromide (0.015 mol) prepared beforehand in diethyl ether is added over approximately 1 h. At the end of the addition, the reaction medium is kept stirred at between –10° C. and 0° C. for approximately 3 h and then it is poured onto a saturated aqueous ammonium chloride solution. The aqueous phase is extracted several times with CH$_2$Cl$_2$ and the organic phases are combined. The resulting organic phase is dried over anhydrous magnesium sulphate and then concentrated.

$^1$H NMR (CDCl$_3$): δ 0.7–1.1 (m, 6H, CH$_3$), 1.1–1.7 (m, 17H, CH$_3$+CH$_2$), 3.1–3.5 (m, 14H, CH$_3$+CH), 4.45–4.85 (several q, 4H, CH) ppm. $^{13}$C NMR (CDCl$_3$): δ 9.65–11.94 (CH$_3$), 16.67–20.06 (CH$_3$), 20.5–20.9 (CH$_2$), 55.06–56.7 (CH$_3$), 60.02–63.05 (CH), 69.05–70.24 (CH), 154.37–155.27 (N—C═N) ppm.

EXAMPLE 27

(S)- and (R)-4-(1-Ethyl-2,2-dimethoxyethylamino)-1,2,4-triazole 1 g of N-(1,2,4-triazol-4-yl)-2,2-dimethoxyethylimine is introduced under nitrogen into 25 ml of dichloroethane in a 100 ml three-necked flask equipped with a magnetic stirrer and a reflux condenser. A solution of ethylmagnesium chloride (0.017 mol) in diethyl ether is added portionwise to this solution, at ambient temperature and with stirring, over 1 h to 2 h approximately. At the end of the addition, the reaction medium is left stirring at ambient temperature for 2 h to 3 h and is then poured onto a saturated ammonium chloride solution. The phases are separated by settling and the aqueous phase is extracted with dichloromethane. The combined organic phases are dried over MgSO$_4$ and concentrated. The residue is purified by flash chromatography on neutral alumina (AcOEt/5% MeOH). 0.50 g of the expected products is obtained.

$^1$H NMR (200 MHz, CDCl$_3$): 0.92 (t, J=7.4 Hz, 3H), 1.36 (m, 2H), 3.01 (m, 1H), 3.36 (s, 3H), 3.40 (s, 3H), 4.19 (d, J=5.6 Hz, 1H), 5.43 (d, NH), 8.17 (s, 2H) ppm. $^{13}$C NMR (200 MHz, CDCl$_3$): 9.67 (CH$_3$), 21.36 (CH$_2$), 55.12 (CH$_3$), 55.75 (CH$_3$), 64.21 (CH), 104.65 (CH), 143.72 (N—C═N) ppm.

The mixture of the stereoisomers is chromatographed on a Chiralcel OD-H® column under the following conditions:
Ambient temperature
Flow rate of 1 ml/min
Mobile phase hexane/isopropanol (60/40)
Separation measured by absorption at 220 nm.

Good separation into two distinct peaks is observed with elution of the (S)-(−)-enantiomer first.
(S)-(−)-Enantiomer:
retention time $t_R$=8.99 min
retention factor k=2.09
(R)-(+)-Enantiomer:
retention time $t_R$=10.68 min
retention factor k=2.67

The mixture of the stereoisomers is also chromatographed on a Chiralcel OD-R® column under the following conditions:
Ambient temperature
Flow rate of 0.5 ml/min
Mobile phase acetonitrile
Separation measured by absorption at 220 nm.

Good separation into two peaks is observed with elution of the (S)-(+)-enantiomer first.
(S)-(+)-Enantiomer:
retention time $t_R$=9.36 min
retention factor k=0.48
(R)-(−)-Enantiomer:
retention time $t_R$=12.21 min
retention factor k=0.93

EXAMPLE 28

(S)- and (R)-4-(1-Isobutyl-2,2-dimethoxyethylamino)-1,2,4-triazole

The compounds are prepared as in Example 27 but using isobutylmagnesium chloride. 0.57 g of the expected compounds is obtained.

$^1$H NMR (200 MHz, CDCl$_3$): 0.83 (2d, J=6.6 Hz, 6H), 1.20 (m, 2H), 1.70 (m, 1H), 3.07 (m, 1H), 3.36 (s, 3H), 3.42 (s, 3H), 4.10 (d, J=4.6 Hz, 1H), 5.24 (d, NH), 8.16 (s, 2H) ppm. $^{13}$C NMR (200 MHz, CDCl$_3$): 22.06 (CH$_3$), 23.27 (CH$_3$), 24.58 (CH), 37.98 (CH$_2$), 55.57 (CH$_3$), 56.20 (CH$_3$), 61.24 (CH), 105.69 (CH), 143.98 (N—C=N) ppm.

The mixture of the stereoisomers is chromatographed on a Chiralcel OD-H® column under the following conditions:
Ambient temperature
Flow rate of 1 ml/min
Mobile phase hexane/isopropanol (90/10)
Separation measured by absorption at 220 nm.

Good separation into two distinct peaks is observed:
retention time $t_{R1}$=19.25 min; $t_R$=23.02 min
retention factor $k_1$=4.96; $k_2$=6.13

EXAMPLE 29

(S)- and (R)-4-(1-Benzyl-2,2-dimethoxyethylamino)-1,2,4-triazole

The compounds are prepared as in Example 27 but using benzylmagnesium chloride. 1 g of the expected compounds is obtained.

$^1$H NMR (200 MHz, CDCl$_3$): 2.8 (m, 2H), 3.35 (m, 1H), 3.44 (s, 3H), 3.48 (s, 3H), 4.25 (d, J=4.6 Hz, 1H), 5.32 (d, NH), 7.18–7.39 (m, 5H$_{aromatic}$), 8.00 (s, 2H) ppm. $^{13}$C NMR (200 MHz, CDCl$_3$): 35.54 (CH$_2$), 55.60 (CH$_3$), 56.04 (CH$_3$), 65.23 (CH), 105.19 (CH), 127.07, 128.88 and 129.18 (CH$_{aromatic}$), 137.10 (C$_{aromatic}$), 143.57 (N—C=N) ppm.

The mixture of the stereoisomers is chromatographed on a Chiralpak AS® column under the following conditions:
Ambient temperature
Flow rate of 1 ml/min
Mobile phase hexane/ethanol (50/50)
Separation measured by absorption at 2,20 nm.

Good separation into two distinct peaks is observed:
retention time $t_{R1}$=8.29 min; $t_R$=11.49 min
retention factor $k_1$=1.74; $k_2$=2.79

EXAMPLE 30

Preparation of the starting N-(1,2,4-triazol-4-yl)-2,2-dimethoxyethylimine of Examples 27, 28 and 29

2 g of 4-amino-1,2,4-triazole (Aldrich) and 4.1 g of a 60% aqueous dimethoxyethanal solution are introduced into a 50 ml round-bottomed flask equipped with a magnetic stirrer and a reflux condenser. This mixture is heated with stirring at a temperature of approximately 100° C. for approximately 2 h. The reaction medium is placed under reduced pressure (P=666.7 Pa) (5 mmHg) and the temperature is increased up to 100° C. The residue is taken up in 30 ml of dichloromethane and an off-white suspension is formed. After drying over anhydrous magnesium sulphate, filtering and concentrating, 3.70 g of the expected product are obtained.

$^1$H NMR (200 MHz, CDCl$_3$): 3.49 (s, 6H), 4.94 (d, J=4.8 Hz, 1H), 8 (d, J=4.8 Hz, 1H), 8.6 (s, 2H) ppm. $^{13}$C NMR (200 MHz, CDCl$_3$): 54.33 (CH$_3$), 101.20 (CH), 138.15 (N—C=N), 155.60 (C=N) ppm.

The invention claimed is:

1. A process for the preparation of a primary amine of formula (I):

wherein
R3 is
a linear or branched alkyl group including from 1 to 6 carbon atoms optionally substituted by one or more hydroxyl groups, amino groups, alkoxy groups including from 1 to 6 carbon atoms or aryl groups including from 6 to 10 carbon atoms, the aryl groups optionally being substituted by one or more linear or branched alkyl groups including from 1 to 6 carbon atoms or by one or more alkoxy groups including from 1 to 6 carbon atoms or by one or more phenyl groups,
a cycloalkyl group including from 5 to 7 carbon atoms optionally substituted by one or more linear or branched alkyl groups including from 1 to 6 carbon atoms or by one or more alkoxy groups including from 1 to 6 carbon atoms,
an aralkyl group including from 7 to 16 carbon atoms optionally substituted by one or more linear or branched alkyl groups including from 1 to 6 carbon atoms, by one or more alkoxy groups including from 1 to 6 carbon atoms or by one or more phenyl groups, comprising the step of reacting a triazolium salt of formula (II):

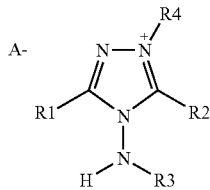
(II)

wherein
R1 and R2, are identical or different, and are
hydrogen,
  a linear or branched alkyl group including from 1 to 6 carbon atoms optionally substituted by one or more alkoxy groups including from 1 to 6 carbon atoms, —(OCH$_2$CH$_2$O)$_n$R''' groups wherein n is an integer ranging from 1 to 4 and R''' is a linear or branched alkyl group including from 1 to 4 carbon atoms, —O-aryl groups including from 6 to 10 carbon atoms optionally substituted by one or more alkoxy groups including from 1 to 6 carbon atoms, linear or branched alkyl groups including from 1 to 6 carbon atoms or phenyl groups, or —O-aralkyl groups including from 7 to 16 carbon atoms optionally substituted by one or more alkoxy groups including from 1 to 6 carbon atoms, linear or branched alkyl groups including from 1 to 6 carbon atoms or phenyl groups;
  an aralkyl group including from 7 to 16 carbon atoms optionally substituted by one or more alkoxy groups including from 1 to 6 carbon atoms, linear or branched alkyl groups including from 1 to 6 carbon atoms or phenyl groups;
  an aryl group including from 6 to 10 carbon atoms optionally substituted by one or more alkoxy groups including from 1 to 6 carbon atoms or linear or branched alkyl groups including from 1 to 6 carbon atoms or phenyl groups,
R4 is
  a linear or branched alkyl group including from 1 to 6 carbon atoms optionally substituted by a —COOH radical or a —COOR''' group in which R''' represents a linear or branched alkyl radical including from 1 to 4 carbon atoms,
  an aralkyl group including from 7 to 16 carbon atoms optionally substituted by one or more alkoxy groups including from 1 to 6 carbon atoms, a linear or branched alkyl groups including from 1 to 6 carbon atoms, a —COOH radical or a —COOR''' group wherein R''' represents a linear or branched alkyl radical including from 1 to 4 carbon atoms,
  a residue of an organic polymer functionalized by an alkylating group,
A is
  a halogen,
  an alkylsulphonate group including from 1 to 6 carbon atoms optionally substituted by one or more halogen groups,
  an arylsulphonate group including from 6 to 10 carbon atoms optionally substituted by one or more halogen groups or linear or branched alkyl groups including from 1 to 4 carbon atoms,
  an alkyl sulphate group including from 1 to 6 carbon atoms,
  a hydrogen sulphate group,
  a hemisulphate group,
  a perchlorate group, or
  a hydroxide group,
with a hydride, to obtain the amine of formula (I).

2. The process according to claim 1, wherein the R3 group comprises an asymmetric carbon α to the nitrogen.

3. The process according to claim 1, wherein the triazolium salt of formula (II) is of the formula (IIa):

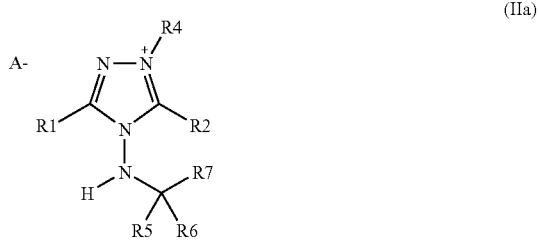
(IIa)

wherein
R5 is
  a hydrogen,
  a linear or branched alkyl group including from 1 to 6 carbon atoms optionally substituted by one or more alkoxy groups including from 1 to 6 carbon atoms, hydroxyl groups or amino groups,
  a cycloalkyl group including from 3 to 7 carbon atoms optionally substituted by one or more alkoxy groups including from 1 to 6 carbon atoms or linear or branched alkyl groups including from 1 to 6 carbon atoms,
  an aryl group including from 6 to 10 carbon atoms optionally substituted by one or more alkoxy groups including from 1 to 6 carbon atoms or linear or branched alkyl groups including from 1 to 6 carbon atoms or phenyl groups,
  an aralkyl group including from 7 to 16 carbon atoms optionally substituted by one or more alkoxy groups including from 1 to 6 carbon atoms, linear or branched alkyl groups including from 1 to 6 carbon atoms or phenyl groups,
R6 is
  a linear or branched alkyl group including from 1 to 6 carbon atoms optionally substituted by one or more alkoxy groups including from 1 to 6 carbon atoms, hydroxyl groups or amino groups,
  a cycloalkyl group including from 3 to 7 carbon atoms optionally substituted by one or more alkoxy groups including from 1 to 6 carbon atoms or linear or branched alkyl groups including from 1 to 6 carbon atoms,
  an aryl group including from 6 to 10 carbon atoms optionally substituted by one or more alkoxy groups including from 1 to 6 carbon atoms or linear or branched alkyl groups including from 1 to 6 carbon atoms or phenyl groups,
  an aralkyl group including from 7 to 16 carbon atoms optionally substituted by one or more alkoxy groups including from 1 to 6 carbon atoms, linear or branched alkyl groups including from 1 to 6 carbon atoms or phenyl groups,
  an aminotriazolium group of formula

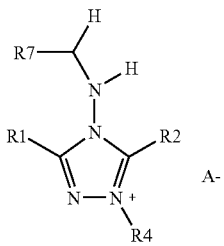

(IIb)

wherein

R7 is a hydrogen, a linear or branched alkyl group including from 1 to 6 carbon atoms optionally substituted by one or more alkoxy groups including from 1 to 6 carbon atoms, hydroxyl groups or amino groups, a cycloalkyl group including from 3 to 7 carbon atoms optionally substituted by one or more alkoxy groups including from 1 to 6 carbon atoms or linear or branched alkyl groups including from 1 to 6 carbon atoms, an aryl group including from 6 to 10 carbon atoms optionally substituted by one or more alkoxy groups including from 1 to 6 carbon atoms or linear or branched alkyl groups including from 1 to 6 carbon atoms or phenyl groups, an aralkyl group including from 7 to 16 carbon atoms optionally substituted by one or more alkoxy groups including from 1 to 6 carbon atoms or linear or branched alkyl groups including from 1 to 6 carbon atoms or phenyl groups, or R5 and R6 can form, together with the carbon atom to which they are bonded, a ring comprising 5 to 7 carbon atoms optionally substituted by one or more alkoxy groups including from 1 to 6 carbon atoms or linear or branched alkyl groups including from 1 to 6 carbon atoms, with the proviso that the carbon carrying the R5, R6 and R7 radicals must be asymmetric.

4. The process according to claim 3, wherein the compound of formula (IIa) is prepared by reaction of a compound of formula (III):

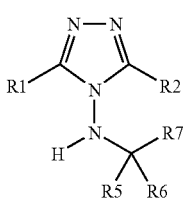

(III)

with an agent for the quaternization of a nitrogen, to produce the compound of formula (IIa).

5. The process according to claim 3, wherein the compound of formula (IIa) is prepared by reaction of a compound of formula (IIIa):

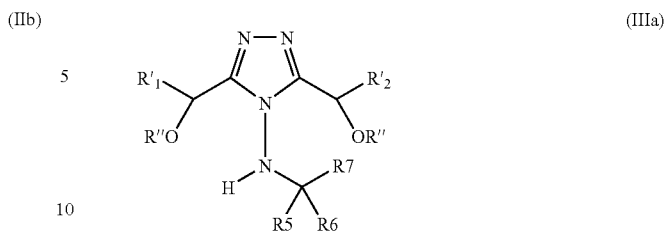

(IIIa)

wherein

R'1 and R'2 are a linear or branched alkyl group including from 1 to 6 carbon atoms optionally substituted by one or more alkoxy groups including from 1 to 6 carbon atoms, an aryl group including from 6 to 10 carbon atoms optionally substituted by one or more alkoxy groups including from 1 to 6 carbon atoms or linear or branched alkyl groups including from 1 to 6 carbon atoms or phenyl groups, or an aralkyl group including from 7 to 16 carbon atoms optionally substituted by one or more alkoxy groups including from 1 to 6 carbon atoms or linear or branched alkyl groups including from 1 to 6 carbon atoms or phenyl groups, and R" represents hydrogen, a linear or branched alkyl group including from 1 to 6 carbon atoms, an aryl group including from 6 to 10 carbon atoms optionally substituted by one or more alkoxy groups including from 1 to 6 carbon atoms or linear or branched alkyl groups including from 1 to 6 carbon atoms or phenyl groups, an aralkyl group including from 7 to 16 carbon atoms optionally substituted by one or more alkoxy groups including from 1 to 6 carbon atoms or linear or branched alkyl groups including from 1 to 6 carbon atoms or phenyl groups, a —$(CH_2CH_2O)_nR'''$ group in which n represents an integer ranging from 1 to 4 and R''' is a linear or branched alkyl group including from 1 to 4 carbon atoms, with an agent for the quaternization of a nitrogen, to produce the compound of formula (IIa).

6. The process according to claim 5, wherein the compound of formula (IIIa) is prepared by reaction of an organometallic compound of formula

R7-M wherein M is an MgX or $CeX_2$ group in which X represents a halogen atom or M represents a metal, with a compound of formula (IV)

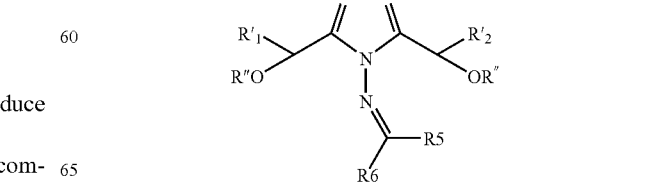

(IV)

with the proviso that, when R" is a hydrogen, at least one of R5 and R6 is an aryl group optionally substituted by one or more alkoxy groups including from 1 to 6 carbon atoms or linear or branched alkyl groups including from 1 to 6 carbon atoms or phenyl groups, to produce the compound of formula (IIIa).

7. The process according to claim 6, wherein the compound of formula (IV) is prepared by etherification and reaction of a compound of formula (V):

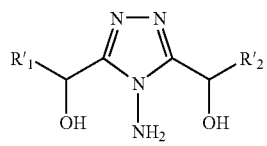

with a compound of formula

O=CR5R6 to produce the compound of formula (IV).

8. The process according to claim 7, wherein the etherification takes place before the reaction of the compound of formula (V) with the compound of formula O=CR5R6.

9. The process according to claim 7, wherein the etherification takes place after the reaction of the compound of formula (V) with the compound of formula O=CR5R6, with the proviso that at least one of R5 and R6 represents an aryl group optionally substituted by one or more alkoxy groups including from 1 to 6 carbon atoms or linear or branched alkyl groups including from 1 to 6 carbon atoms or phenyl groups.

10. The process according to claim 5, wherein the compound of formula (IIIa) is prepared by reduction by the action of a metal hydride on a compound of formula (IV)

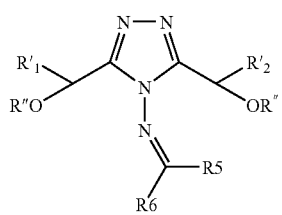

or by hydrogenation of the compound of formula (IV), with the proviso that R5 cannot be hydrogen.

11. An intermediate for preparing an amine of formula $H_2N$—CHR6R7, wherein

R6 is
- a linear or branched alkyl group including from 1 to 6 carbon atoms optionally substituted by one or more alkoxy groups including from 1 to 6 carbon atoms, hydroxyl groups or amino groups,
- a cycloalkyl group including from 3 to 7 carbon atoms optionally substituted by one or more alkoxy groups including from 1 to 6 carbon atoms or linear or branched alkyl groups including from 1 to 6 carbon atoms,
- an aryl group including from 6 to 10 carbon atoms optionally substituted by one or more alkoxy groups including from 1 to 6 carbon atoms or linear or branched alkyl groups including from 1 to 6 carbon atoms or phenyl groups,
- an aralkyl group including from 7 to 16 carbon atoms optionally substituted by one or more alkoxy groups including from 1 to 6 carbon atoms, linear or branched alkyl groups including from 1 to 6 carbon atoms or phenyl groups, an aminotriazolium group of formula

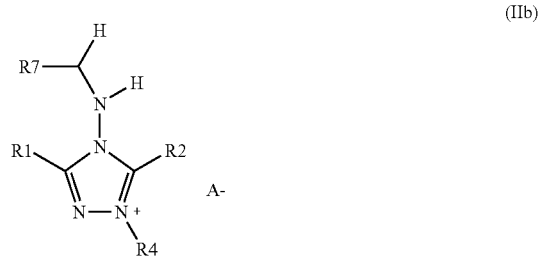

wherein R1 and R2, are identical or different, and are
- hydrogen,
- a linear or branched alkyl group including from 1 to 6 carbon atoms optionally substituted by one or more alkoxy groups including from 1 to 6 carbon atoms, —(OCH$_2$CH$_2$O)$_n$R''' groups wherein n is an integer ranging from 1 to 4 and R''' is a linear or branched alkyl group including from 1 to 4 carbon atoms, —O-aryl groups including from 6 to 10 carbon atoms optionally substituted by one or more alkoxy groups including from 1 to 6 carbon atoms, linear or branched alkyl groups including from 1 to 6 carbon atoms or phenyl groups, or —O-aralkyl groups including from 7 to 16 carbon atoms optionally substituted by one or more alkoxy groups including from 1 to 6 carbon atoms, linear or branched alkyl groups including from 1 to 6 carbon atoms or phenyl groups:
- an aralkyl group including from 7 to 16 carbon atoms optionally substituted by one or more alkoxy groups including from 1 to 6 carbon atoms, linear or branched alkyl groups including from 1 to 6 carbon atoms or phenyl groups;
- an aryl group including from 6 to 10 carbon atoms optionally substituted by one or more alkoxy groups including from 1 to 6 carbon atoms or linear or branched alkyl groups including from 1 to 6 carbon atoms or phenyl groups, R4 is
- a linear or branched alkyl group including from 1 to 6 carbon atoms optionally substituted by a —COOH radical or a —COOR''' group in which R''' represents a linear or branched alkyl radical including from 1 to 4 carbon atoms,
- an aralkyl group including from 7 to 16 carbon atoms optionally substituted by one or more alkoxy groups including from 1 to 6 carbon atoms, a linear or branched alkyl groups including from 1 to 6 carbon atoms, a —COOH radical or a —COOR''' group wherein R''' represents a linear or branched alkyl radical including from 1 to 4 carbon atoms, or
- a residue of an organic polymer functionalized by an alkylating group, and A is
 a halogen,
 an alkylsulphonate group including from 1 to 6 carbon atoms optionally substituted by one or more halogen groups,
 an arylsulphonate group including from 6 to 10 carbon atoms optionally substituted by one or more halogen groups or linear or branched alkyl groups including from 1 to 4 carbon atoms,
 an alkyl sulphate group including from 1 to 6 carbon atoms,
 a hydrogen sulphate group,
 a hemisulphate group,
 a perchlorate group, or
 a hydroxide group,
R7 is
 a hydrogen,
 a linear or branched alkyl group including from 1 to 6 carbon atoms optionally substituted by one or more alkoxy groups including from 1 to 6 carbon atoms, hydroxyl groups or amino groups,
 a cycloalkyl group including from 3 to 7 carbon atoms optionally substituted by one or more alkoxy groups including from 1 to 6 carbon atoms or linear or branched alkyl groups including from 1 to 6 carbon atoms,
 an aryl group including from 6 to 10 carbon atoms optionally substituted by one or more alkoxy groups including from 1 to 6 carbon atoms or linear or branched alkyl groups including from 1 to 6 carbon atoms or phenyl groups,
 an aralkyl group including from 7 to 16 carbon atoms optionally substituted by one or more alkoxy groups including from 1 to 6 carbon atoms or linear or branched alkyl groups including from 1 to 6 carbon atoms or phenyl groups,
wherein the intermediate is selected from the group consisting of:
 4-[(R)-1-Ethyl-2,2-dimethoxyethylamino]-(S,S)-3,5-bis(1-methoxyethyl)-1,2,4-triazole
 4-[(S)-1-Ethyl-2,2-dimethoxyethylamino]-(S,S)-3,5-bis(1-ethoxyethyl)-1,2,4-triazole
 4-[(R)-1-Ethyl-2,2-dimethoxyethylamino]-(S,S)-3,5-bis(1-ethoxyethyl)-1,2,4-triazole
 4-(1-Phenyl-2,2-dimethoxyethylamino)-(S,S)-3,5-bis(1-methoxyethyl)-1,2,4-triazole
 4-(1-Ethyl-2,2-dimethoxyethylamino)-(S,S)-3,5-bis(1-(2-methoxyethyl)ethyl)-1,2,4-triazole
 4-(1-Ethylbutylamino)-(S,S)-3,5-bis(1-methoxyethyl)-1,2,4-triazole
 4-(1-Ethylisobutylamino)-(S,S)-3,5-bis(1-methoxyethyl)-1,2,4-triazole
 4-(1-Phenylpropylamino)-(S,S)-3,5-bis(1-methoxyethyl)-1,2,4-triazole
 4-(1-Phenylethylamino)-(S,S)-3,5-bis(1-methoxyethyl)-1,2,4-triazole and
 (Hexyl-3,4-diamino)-4,4'-bis[(S,S)-3,5-bis(1-methoxyethyl)-1,2,4-triazole].

12. An intermediate for preparing an amine of formula H$_2$N—CR5R6R7 wherein
 R5 is
  a hydrogen,
  a linear or branched alkyl group including from 1 to 6 carbon atoms optionally substituted by one or more alkoxy groups including from 1 to 6 carbon atoms, hydroxyl groups or amino groups,
  a cycloalkyl group including from 3 to 7 carbon atoms optionally substituted by one or more alkoxy groups including from 1 to 6 carbon atoms or linear or branched alkyl groups including from 1 to 6 carbon atoms,
  an aryl group including from 6 to 10 carbon atoms optionally substituted by one or more alkoxy groups including from 1 to 6 carbon atoms or linear or branched alkyl groups including from 1 to 6 carbon atoms or phenyl groups,
  an aralkyl group including from 7 to 16 carbon atoms optionally substituted by one or more alkoxy groups including from 1 to 6 carbon atoms, linear or branched alkyl groups including from 1 to 6 carbon atoms or phenyl groups,
 R6 is
  a linear or branched alkyl group including from 1 to 6 carbon atoms optionally substituted by one or more alkoxy groups including from 1 to 6 carbon atoms, hydroxyl groups or amino groups,
  a cycloalkyl group including from 3 to 7 carbon atoms optionally substituted by one or more alkoxy groups including from 1 to 6 carbon atoms or linear or branched alkyl groups including from 1 to 6 carbon atoms,
  an aryl group including from 6 to 10 carbon atoms optionally substituted by one or more alkoxy groups including from 1 to 6 carbon atoms or linear or branched alkyl groups including from 1 to 6 carbon atoms or phenyl groups,
  an aralkyl group including from 7 to 16 carbon atoms optionally substituted by one or more alkoxy groups including from 1 to 6 carbon atoms, linear or branched alkyl groups including from 1 to 6 carbon atoms or phenyl groups,
  an aminotriazolium group of formula

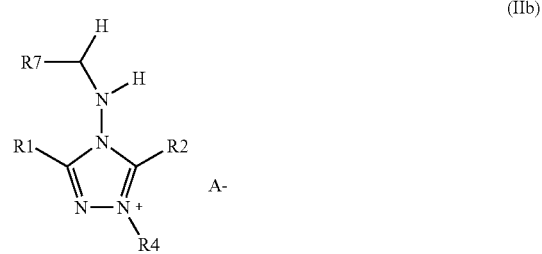

(IIb)

wherein R1 and R2, are identical or different, and are
 hydrogen,
 a linear or branched alkyl group including from 1 to 6 carbon atoms optionally substituted by one or more alkoxy groups including from 1 to 6 carbon atoms, —(OCH$_2$CH$_2$O)$_n$R''' groups wherein n is an integer ranging from 1 to 4 and R''' is a linear or branched alkyl group including from 1 to 4 carbon atoms, —O-aryl groups including from 6 to 10 carbon atoms optionally substituted by one or more alkoxy groups including from 1 to 6 carbon atoms, linear or branched alkyl groups including from 1 to 6 carbon atoms or phenyl groups, or —O-aralkyl groups including from 7 to 16 carbon atoms optionally substituted by one or more alkoxy groups including from 1 to 6 carbon atoms, linear or branched alkyl groups including from 1 to 6 carbon atoms or phenyl groups;
 an aralkyl group including from 7 to 16 carbon atoms optionally substituted by one or more alkoxy groups including from 1 to 6 carbon atoms, linear or branched alkyl groups including from 1 to 6 carbon atoms or phenyl groups;

an aryl group including from 6 to 10 carbon atoms optionally substituted by one or more alkoxy groups including from 1 to 6 carbon atoms or linear or branched alkyl groups including from 1 to 6 carbon atoms or phenyl groups, R4 is
a linear or branched alkyl group including from 1 to 6 carbon atoms optionally substituted by a —COOH radical or a —COOR'" group in which R'" represents a linear or branched alkyl radical including from 1 to 4 carbon atoms, an aralkyl group including from 7 to 16 carbon atoms optionally substituted by one or more alkoxy groups including from 1 to 6 carbon atoms, a linear or branched alkyl groups including from 1 to 6 carbon atoms, a —COOH radical or a —COOR'" group wherein R'" represents a linear or branched alkyl radical including from 1 to 4 carbon atoms, or a residue of an organic polymer functionalized by an alkylating group, and A is
a halogen,
an alkylsulphonate group including from 1 to 6 carbon atoms optionally substituted by one or more halogen groups,
an arylsulphonate group including from 6 to 10 carbon atoms optionally substituted by one or more halogen groups or linear or branched alkyl groups including from 1 to 4 carbon atoms,
an alkyl sulphate group including from 1 to 6 carbon atoms,
a hydrogen sulphate group,
a hemisulphate group,
a perchlorate group, or
a hydroxide group, R7 is
a hydrogen,
a linear or branched alkyl group including from 1 to 6 carbon atoms optionally substituted by one or more alkoxy groups including from 1 to 6 carbon atoms, hydroxyl groups or amino groups,
a cycloalkyl group including from 3 to 7 carbon atoms optionally substituted by one or more alkoxy groups including from 1 to 6 carbon atoms or linear or branched alkyl groups including from 1 to 6 carbon atoms,
an aryl group including from 6 to 10 carbon atoms optionally substituted by one or more alkoxy groups including from 1 to 6 carbon atoms or linear or branched alkyl groups including from 1 to 6 carbon atoms or phenyl groups,
an aralkyl group including from 7 to 16 carbon atoms optionally substituted by one or more alkoxy groups including from 1 to 6 carbon atoms or linear or branched alkyl groups including from 1 to 6 carbon atoms or phenyl groups, or R5 and R6 can form, together with the carbon atom to which they are bonded, a ring comprising 5 to 7 carbon atoms optionally substituted by one or more alkoxy groups including from 1 to 6 carbon atoms or linear or branched alkyl groups including from 1 to 6 carbon atoms, wherein the intermediate is selected from the group consisting of:

N-[(S,S)-3,5-Bis(1-methoxyethyl)-1,2,4-triazol-4-yl]-2,2-dimethoxyethylimine

N-[(S,S)-3,5-Bis(1-methoxyethyl)-1,2,4-triazol-4-yl] butylimine

N-[(S,S)-3,5-Bis(1-methoxyethyl)-1,2,4-triazol-4-yl] isobutylimine

N-[(S,S)-3,5-Bis(1-methoxyethyl)-1,2,4-triazol-4-yl]-1-(ethoxycarbonyl)methylimine N-[(S,S)-3,5-Bis(1-methoxyethyl)-1,2,4-triazol-4-yl]-1-phenylethylimine N-[(S,S)-3,5-Bis(1-methoxyethyl)-1,2,4-triazol-4-yl]-1-methyl-2,2-dimethoxyethylimine Bis[N-[(S,S)-3,5-bis(1-methoxyethyl)-1,2,4-triazol-4-yl]methylimine]

N-[(S,S)-3,5-Bis(1-ethoxyethyl)-1,2,4-triazol-4-yl]-2,2-dimethoxyethylimine, and N-[(S,S)-3,5-Bis(1-(2-methoxyethoxy)ethyl)-1,2,4-triazol-4-yl]-2,2-dimethoxyethylimine.

13. The process according to claim 4, wherein the stereoisomers of formula (III) are separated by high performance liquid chromatography.

14. The process according to claim 3, wherein the diastereoisomers of formula (IIa) are separated by crystallization.

15. An enantiomerically pure diastereoisomer of a compound of formula (IIa)

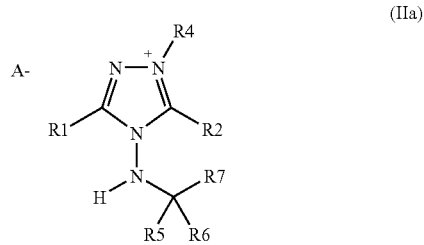

(IIa)

wherein
R1 and R2, are identical or different, and are
hydrogen,
a linear or branched alkyl group including from 1 to 6 carbon atoms optionally substituted by one or more alkoxy groups including from 1 to 6 carbon atoms, —(OCH$_2$CH$_2$O)$_n$R'" groups wherein n is an integer ranging from 1 to 4 and R'" is a linear or branched alkyl group including from 1 to 4 carbon atoms, —O-aryl groups including from 6 to 10 carbon atoms optionally substituted by one or more alkoxy groups including from 1 to 6 carbon atoms, linear or branched alkyl groups including from 1 to 6 carbon atoms or phenyl groups, or —O-aralkyl groups including from 7 to 16 carbon atoms optionally substituted by one or more alkoxy groups including from 1 to 6 carbon atoms, linear or branched alkyl groups including from 1 to 6 carbon atoms or phenyl groups;

an aralkyl group including from 7 to 16 carbon atoms optionally substituted by one or more alkoxy groups including from 1 to 6 carbon atoms, linear or branched alkyl groups including from 1 to 6 carbon atoms or phenyl groups;

an aryl group including from 6 to 10 carbon atoms optionally substituted by one or more alkoxy groups including from 1 to 6 carbon atoms or linear or branched alkyl groups including from 1 to 6 carbon atoms or phenyl groups, R4 is
a linear or branched alkyl group including from 1 to 6 carbon atoms optionally substituted by a —COOH radical or a —COOR'" group in which R'" represents a linear or branched alkyl radical including from 1 to 4 carbon atoms, an aralkyl group including from 7 to 16 carbon atoms optionally substituted by one or more alkoxy groups including from 1 to 6 carbon atoms, a linear or branched alkyl groups including from 1 to 6 carbon atoms, a —COOH radical or a —COOR'" group wherein R'" represents a linear or branched alkyl radical including from 1 to 4 carbon atoms, a residue of an organic polymer functionalized by an alkylating group, A is a halogen, an alkylsulphonate group including from 1 to 6 carbon atoms optionally substituted by one or more halogen groups, an arylsulphonate group including from 6 to 10 carbon atoms optionally substituted by one or more halogen groups or linear or branched alkyl groups including from 1 to 4 carbon atoms, an alkyl sulphate group including from 1 to 6 carbon atoms, a hydrogen sulphate group, a hemisulphate group, a perchlorate group, or a hydroxide group, R5 is a hydrogen, a linear or branched alkyl group including from 1 to 6 carbon atoms optionally substituted by one or more alkoxy groups including from 1 to 6 carbon atoms, hydroxyl groups or amino groups, a cycloalkyl group including from 3 to 7 carbon atoms optionally substituted by one or more alkoxy groups including from 1 to 6 carbon atoms or linear or branched alkyl groups including from 1 to 6 carbon atoms, an aryl group including from 6 to 10 carbon atoms optionally substituted by one or more alkoxy groups including from 1 to 6 carbon atoms or linear or branched alkyl groups including from 1 to 6 carbon atoms or phenyl groups, an aralkyl group including from 7 to 16 carbon atoms optionally substituted by one or more alkoxy groups including from 1 to 6 carbon atoms, linear or branched alkyl groups including from 1 to 6 carbon atoms or phenyl groups, R6 is a linear or branched alkyl group including from 1 to 6 carbon atoms optionally substituted by one or more alkoxy groups including from 1 to 6 carbon atoms, hydroxyl groups or amino groups, a cycloalkyl group including from 3 to 7 carbon atoms optionally substituted by one or more alkoxy groups including from 1 to 6 carbon atoms or linear or branched alkyl groups including from 1 to 6 carbon atoms, an aryl group including from 6 to 10 carbon atoms optionally substituted by one or more alkoxy groups including from 1 to 6 carbon atoms or linear or branched alkyl groups including from 1 to 6 carbon atoms or phenyl groups, an aralkyl group including from 7 to 16 carbon atoms optionally substituted by one or more alkoxy groups including from 1 to 6 carbon atoms, linear or branched alkyl groups including from 1 to 6 carbon atoms or phenyl groups, R7 is a hydrogen, a linear or branched alkyl group including from 1 to 6 carbon atoms optionally substituted by one or more alkoxy groups including from 1 to 6 carbon atoms, hydroxyl groups or amino groups, a cycloalkyl group including from 3 to 7 carbon atoms optionally substituted by one or more alkoxy groups including from 1 to 6 carbon atoms or linear or branched alkyl groups including from 1 to 6 carbon atoms, an aryl group including from 6 to 10 carbon atoms optionally substituted by one or more alkoxy groups including from 1 to 6 carbon atoms or linear or branched alkyl groups including from 1 to 6 carbon atoms or phenyl groups, an aralkyl group including from 7 to 16 carbon atoms optionally substituted by one or more alkoxy groups including from 1 to 6 carbon atoms or linear or branched alkyl groups including from 1 to 6 carbon atoms or phenyl groups, or R5 and R6 can form, together with the carbon atom to which they are bonded, a ring comprising 5 to 7 carbon atoms optionally substituted by one or more alkoxy groups including from 1 to 6 carbon atoms or linear or branched alkyl groups including from 1 to 6 carbon atoms.

16. The enantiomerically pure diastereoisomer of a compound of formula (IIa) according to claim 15, wherein the compound of formula (IIa) is 1-benzyl-4-[(R)-1-phenyl-2,2-dimethoxyethylamino]-(S,S)-3,5-bis(1-methoxyethyl)-1,2,4-triazolium bromide.

17. The process according to claim 1, further comprising the step of isolating the amine of formula (I).

18. The process according to claim 4, wherein the compound of formula (IIa) is isolated.

19. The process according to claim 5, wherein the compound of formula (IIa) is isolated.

20. The process according to claim 6, wherein M is Li, Cu or (½) Zn.

21. The process according to claim 6, wherein the compound of formula (IIIa) is isolated.

22. The process according to claim 7, wherein the compound of formula (IV) is isolated.

23. The process according to claim 5, wherein the stereoisomers of formula (IIIa) are separated by high performance liquid chromatography.

24. The process according to claim 13, wherein the high performance liquid chromatography is chiral high performance liquid chromatography.

25. The process according to claim 23, wherein the high performance liquid chromatography is chiral high performance liquid chromatography.

26. The process according to claim 5, wherein the diastereoisomers of formula (IIa) are separated by crystallization.

* * * * *